US012636380B2

(12) United States Patent
Li et al.

(10) Patent No.: US 12,636,380 B2
(45) Date of Patent: May 26, 2026

(54) METHODS AND COMPOSITIONS FOR INCREASING TRANSDUCTION EFFICIENCY WITH CELL MEMBRANE FUSION PROTEINS

(71) Applicants: The University of North Carolina at Chapel Hill, Chapel Hill, NC (US); TEXAS TECH UNIVERSITY SYSTEM, Lubbock, TX (US)

(72) Inventors: Chengwen Li, Chapel Hill, NC (US); R. Bryan Sutton, Lubbock, TX (US)

(73) Assignees: The University of North Carolina at Chapel Hill, Chapel Hill, NC (US); Texas Tech University System, Lubbock, TX (US)

( * ) Notice: Subject to any disclaimer, the term of this patent is extended or adjusted under 35 U.S.C. 154(b) by 859 days.

(21) Appl. No.: 17/756,273

(22) PCT Filed: Nov. 20, 2020

(86) PCT No.: PCT/US2020/061420
§ 371 (c)(1),
(2) Date: May 20, 2022

(87) PCT Pub. No.: WO2021/102215
PCT Pub. Date: May 27, 2021

(65) Prior Publication Data
US 2022/0347315 A1 Nov. 3, 2022

Related U.S. Application Data

(60) Provisional application No. 62/939,344, filed on Nov. 22, 2019.

(51) Int. Cl.
*A61K 48/00* (2006.01)
*C12N 15/86* (2006.01)
(52) U.S. Cl.
CPC .......... *A61K 48/0008* (2013.01); *C12N 15/86* (2013.01); *C12N 2750/14143* (2013.01)
(58) Field of Classification Search
None
See application file for complete search history.

(56) References Cited

U.S. PATENT DOCUMENTS

| | | | |
|---|---|---|---|
| 8,697,439 B2 | 4/2014 | Mangeot et al. | |
| 10,301,648 B2 | 5/2019 | Vandenberghe et al. | |
| 10,494,645 B2 | 12/2019 | Auricchio et al. | |
| 2003/0211590 A1 | 11/2003 | Hwu | |
| 2010/0266551 A1 | 10/2010 | Richard et al. | |
| 2020/0078473 A1 | 3/2020 | Lochmuller et al. | |

FOREIGN PATENT DOCUMENTS

| | | | | |
|---|---|---|---|---|
| WO | 2012109214 A1 | 8/2012 | | |
| WO | WO-2017218866 A1 * | 12/2017 | ............. | A61P 21/00 |
| WO | WO-2018055060 A1 * | 3/2018 | ............. | A61P 43/00 |

OTHER PUBLICATIONS

Liu, et al. "Enhancing gene delivery of adeno-associated viruses by cell-permeable peptides." Molecular therapy-methods and Clinical Development. vol. 1 No. 12 2014. (Year: 2014).*

Schoen, et al. "Gene transfer mediated by fusion protein hemagglutinin reconstituted in cationic lipid vesicles." Gene therapy. vol. 6 1999. (Year: 1999).*

Harsini, et al. FerA is a membrane-associating four-helix bundle domain in the ferlin family of membrane-fusion proteins. Scientific Reports. 2018; 8:1-11. (Year: 2018).*

Peulen, et al. Ferlin overview: From membrane to cancer biology. Cells. 2019; 8(9):954 (Year: 2019).*

Cooper and Head. Membrane injury and repair in the muscular dystrophies. The Neuroscientist. 2015; 21(6):653-68. (Year: 2015).*

International Search Report and Written Opinion corresponding to PCT/US2020/061420; mailed Mar. 16, 2021.

"International Preliminary Report on Patentability corresponding to PCT/US2020/061420; mailed Jun. 2, 2022".

Harsini, Faraz M., et al., "FerA is a Membrane-Associating Four-Helix Bundle Domain in the Ferlin Family of Membrane-Fusion Proteins", Scientific Reports, 8(Article No. 10949), 2018, 1-11.

Liu, Yarong , et al., "Enhancing gene delivery of adeno-associated viruses by cell-permeable peptides", Molecular Therapy—Methods & Clinical Development, 1, 2014, 1-13.

Schoen, P., et al., "Gene transfer mediated by fusion protein hemagglutinin reconstituted in cationic lipid vesicles", Gene Therapy, 6, 1999, 823-832.

Zhang, Xintao , et al., "Membrane fusion FerA domains enhance adeno-associated virus vector transduction", Biomaterials, 241(Article No. 119906), 2020, 1-12.

Krahn, Martin, et al., "A Naturally Occurring Human Minidysferlin Protein Repairs Sarcolemmal Lesions in a Mouse Model of Dysferlinopathy", Science Translational Medicine 2(50):50ra69 DOI: 10.1126/scitranslmed.3000951 (Sep. 22, 2010) 9 pages.

Liu, Yarong, et al., "Enhancing gene delivery of adeno-associated viruses by cell-permeable peptides", Molecular Therapy—Methods & Clinical Development 1(12): doi:10.1038/mtm.2013.12 (Feb. 19, 2014) 25 pages.

Sondergaard, Patricia C, et al., "AAV.Dysferlin Overlap Vectors Restore Function in Dysferlinopathy Animal Models", Ann Clin Transl Neurol. 2(3):256-270 (Mar. 2015).

* cited by examiner

Primary Examiner — Allison M Fox
Assistant Examiner — Gina Pronzati
(74) Attorney, Agent, or Firm — Myers Bigel, P.A.

(57) ABSTRACT

The invention relates to methods and compositions for increasing introduction (e.g., transduction) efficiency. In particular, the invention relates to methods of increasing introduction (e.g., transduction) efficiency by contacting a host cell with a heterologous agent in the presence of a cell membrane fusion protein or a functional fragment or derivative thereof. The invention further relates to compositions that include a heterologous agent and a cell membrane fusion protein or a functional fragment or derivative thereof.

18 Claims, 20 Drawing Sheets

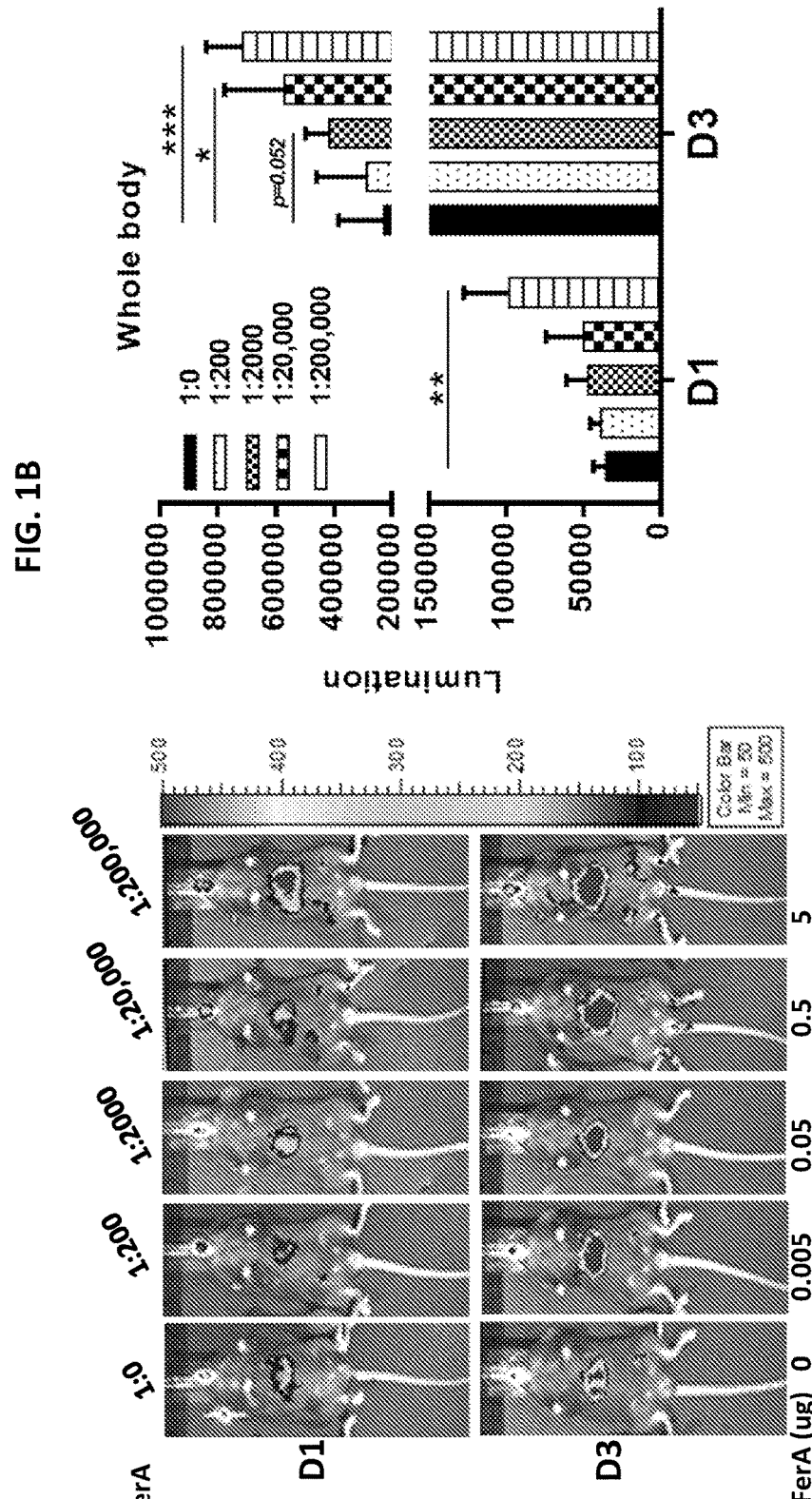

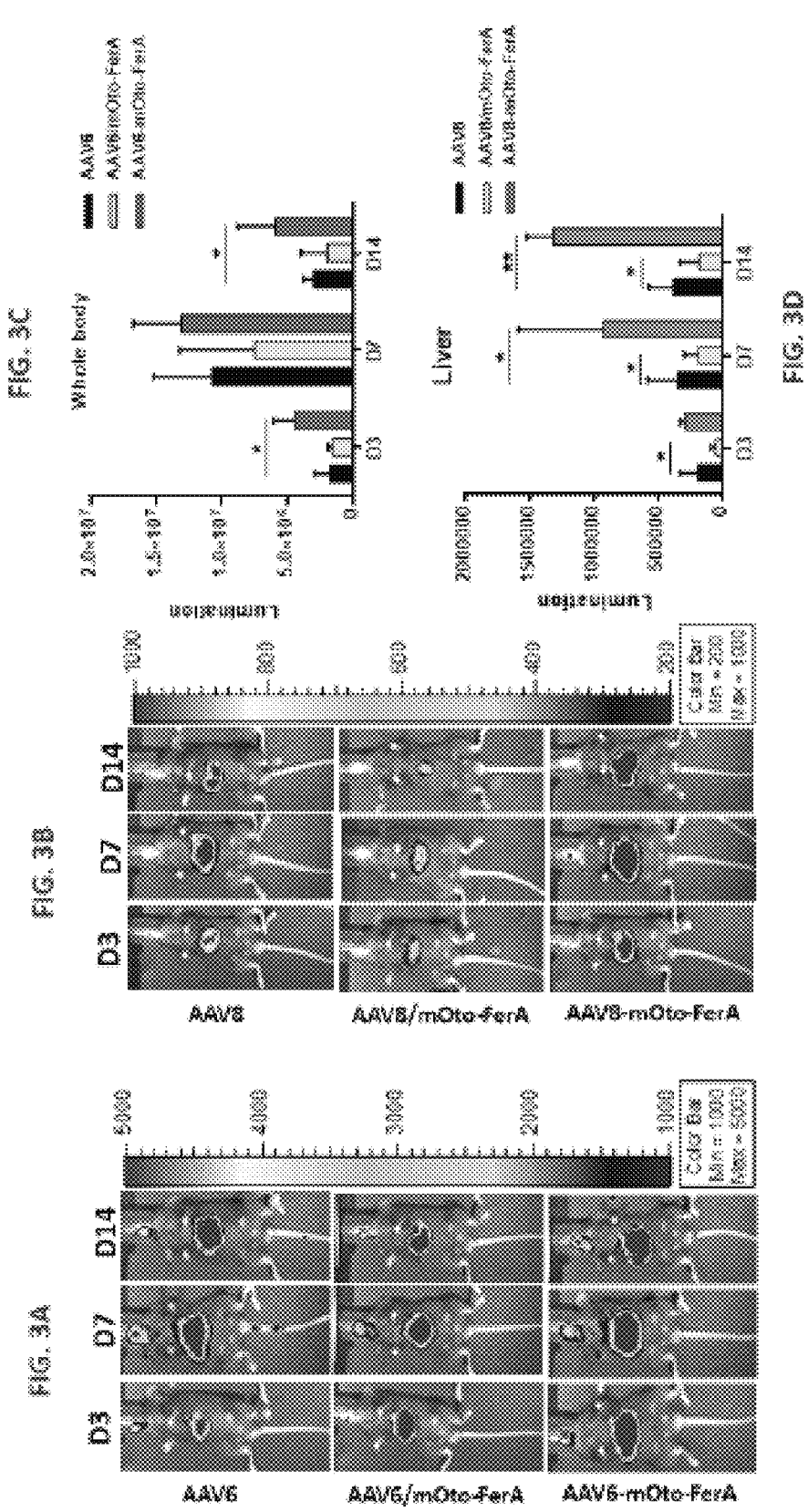

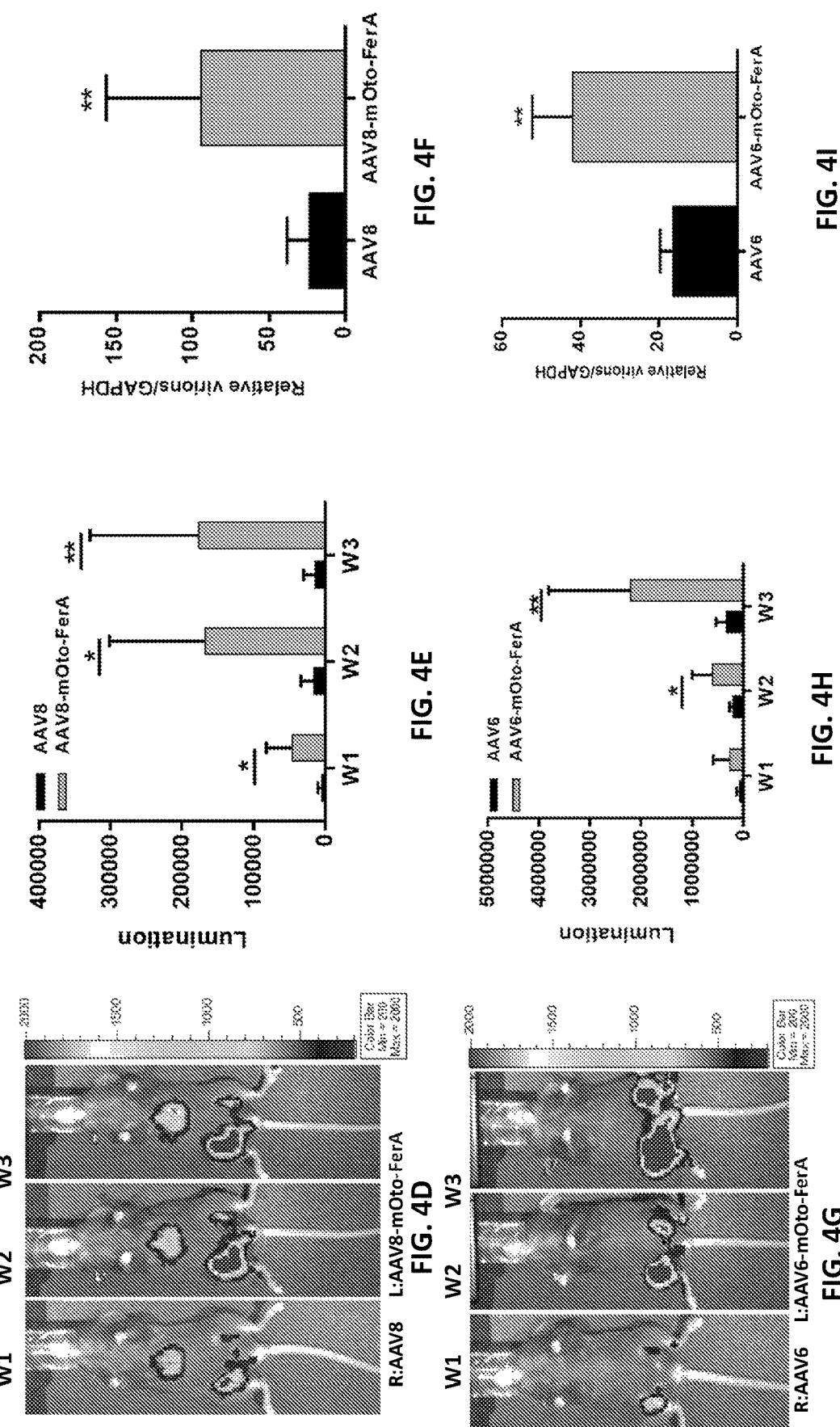

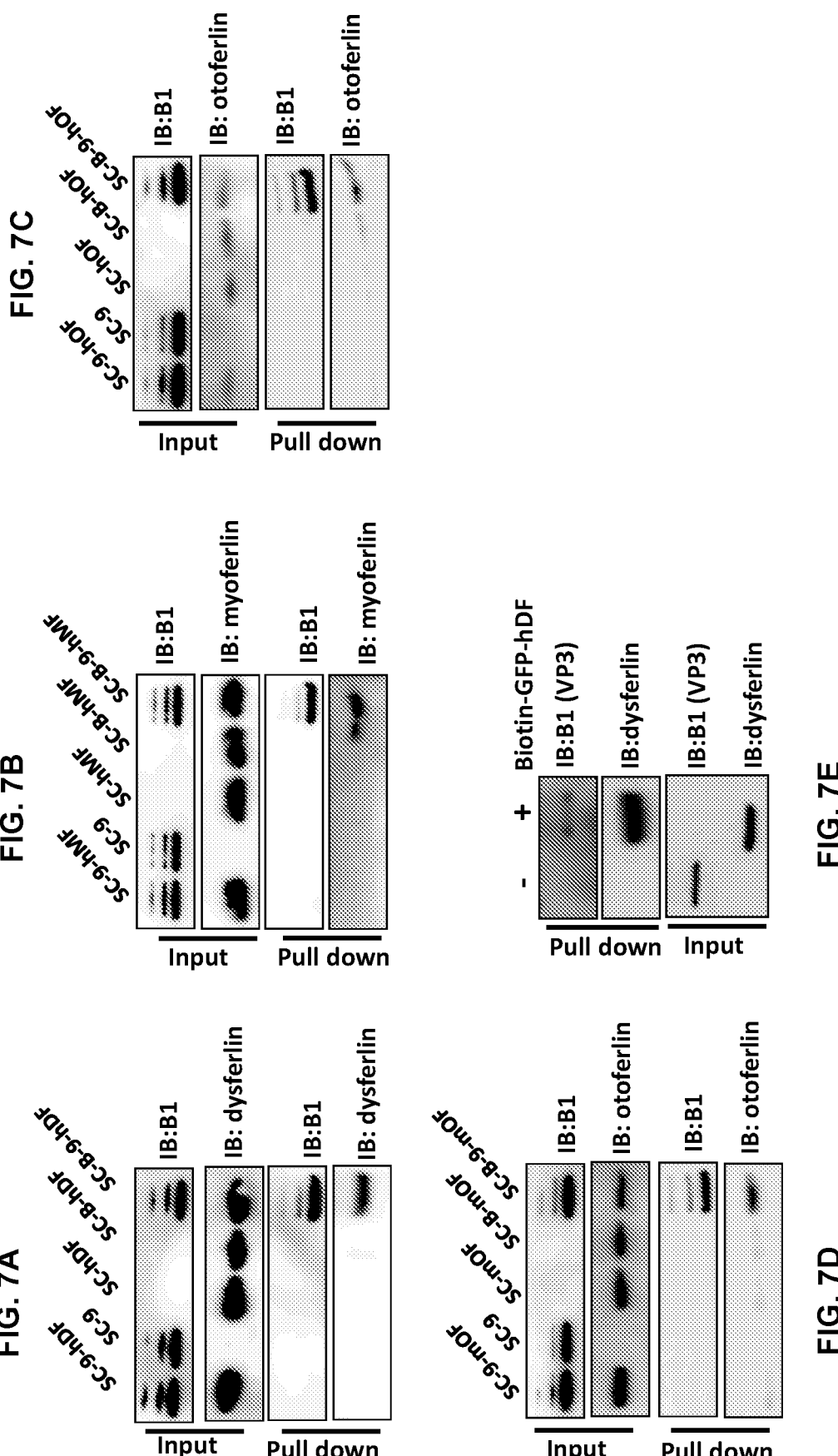

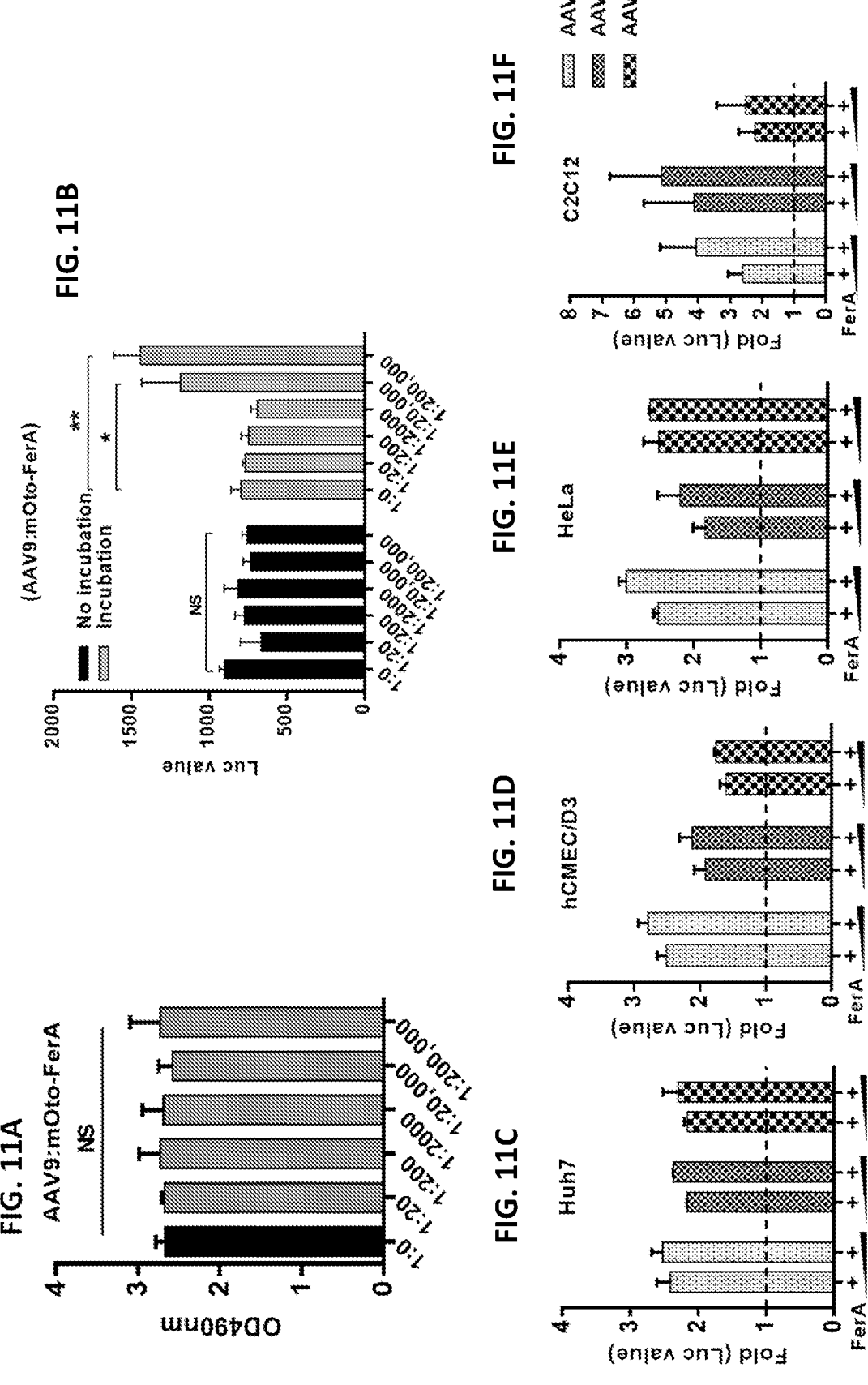

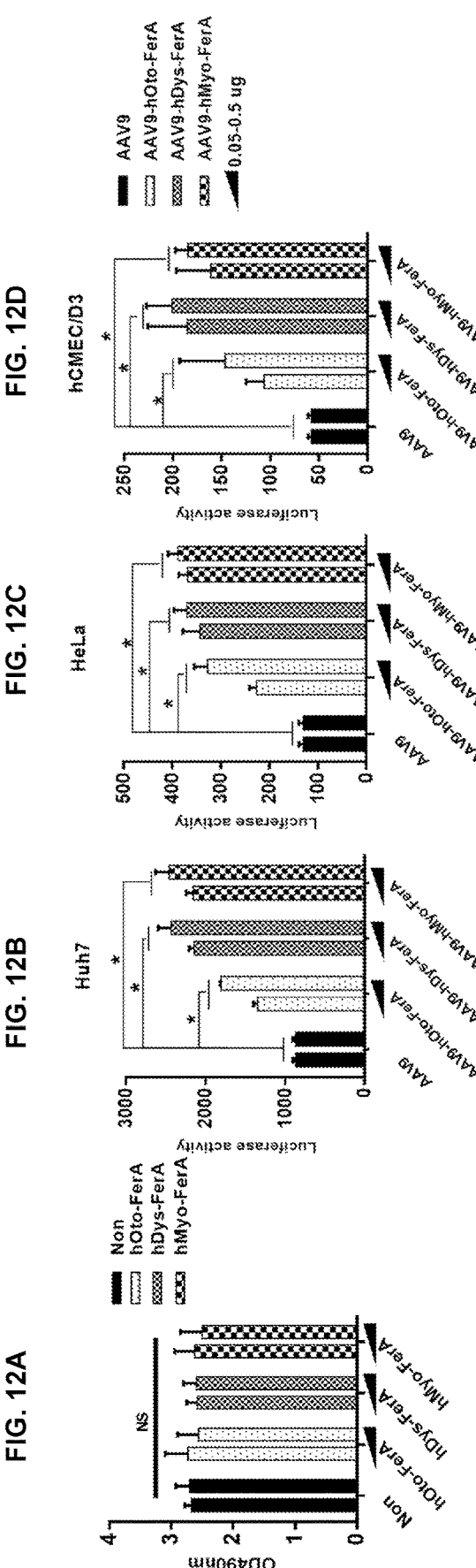

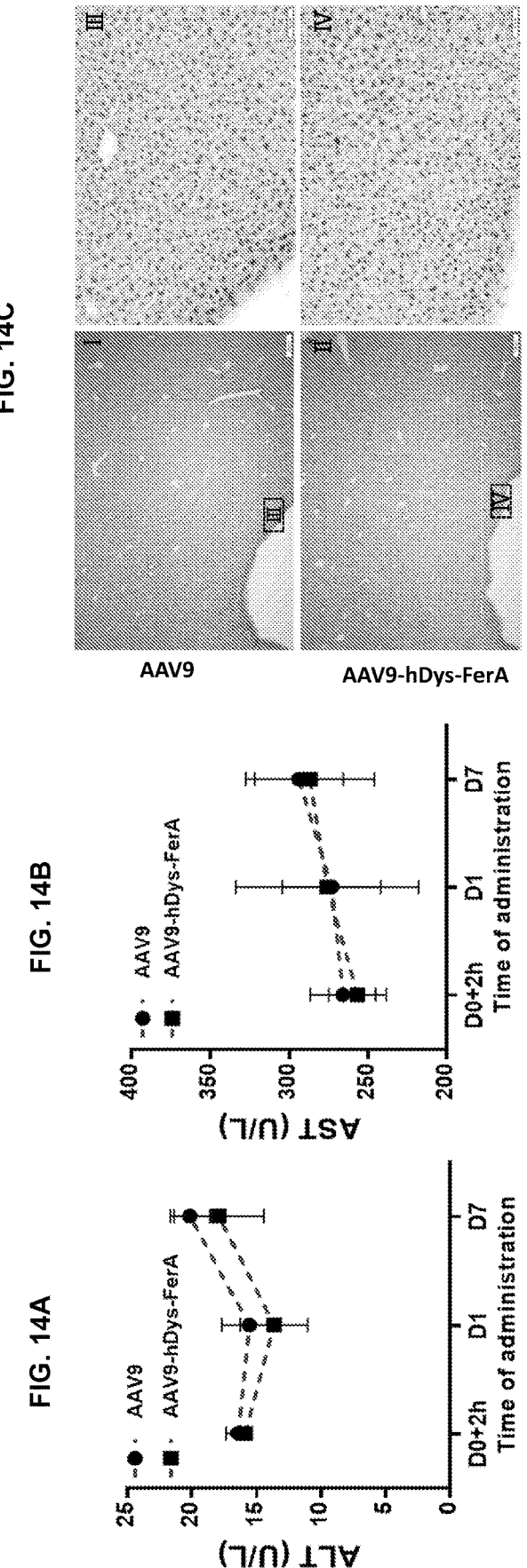

METHODS AND COMPOSITIONS FOR INCREASING TRANSDUCTION EFFICIENCY WITH CELL MEMBRANE FUSION PROTEINS

STATEMENT OF PRIORITY

This application is a 35 U.S.C. § 371 national phase application of PCT Application PCT/US2020/061420, filed Nov. 20, 2020, which claims the benefit of U.S. Provisional Application Ser. No. 62/939,344, filed Nov. 22, 2019, the entire contents of each of which are incorporated by reference herein.

GOVERNMENT SUPPORT

This invention was made with government support under Grant Numbers AI117408, HL144661, HL125749, and AR063634 awarded by the National Institutes of Health. The government has certain rights in the invention.

FIELD OF THE INVENTION

This invention relates to methods and compositions for gene therapy. In particular, the invention relates to methods and compositions for introducing (e.g., transducing) a heterologous agent into a host cell comprising contacting the host cell with the heterologous agent in the presence of a cell membrane fusion protein or a functional fragment or derivative thereof.

BACKGROUND OF THE INVENTION

Approximately 1 in 10 people in the US suffers from a rare genetic disease, which can seriously impact life-span, quality of life, independence, and economic potential. Gene therapy is the most promising form of treatment for the correction of heritable diseases. Among gene therapy delivery vehicles, adeno-associated virus (AAV) vectors have showed therapeutic effect in numerous clinical trials. Currently, 13 serotypes and numerous AAV variants and mutants have been isolated and studied as gene delivery vehicles. Several AAV serotypes, such as AAV2, AAV8, and AAV9, have been extensively employed in clinical trials and achieved therapeutic effects. Despite clinical success, emerging concerns about limited transduction efficacy and the high vector dose requirement remain crucial barriers for ongoing AAV-based gene therapy in preclinical and clinical settings. Data from AAV-human factor IX (hFIX)-related clinical trials in hemophilia B patients have shown that high vector dose directly correlates with the cellular immune responses to vector capsids. Meanwhile, several studies have demonstrated that AAV capsid or transgene-specific cytotoxic T lymphocyte (CTL) response and late innate immune activation after long-term AAV transduction hinder AAV transduction efficiency, which could be strengthened under the condition of high dose of vectors. In this context, tremendous efforts have been directed to improve the AAV transduction efficacy while simultaneously decreasing the vector dose. Several approaches, including but not limited to capsid/genome engineering and polyploid AAV capsid modification, have been undertaken in an effort to produce and impel AAV variants into desired tissues or cell types and achieve therapeutic efficacy. Additionally, covalent coupling of targeting ligands to intact AAV particles and magnetically guided AAV delivery systems have been exploited to achieve selective gene transfer in distinct cell types, even in non-permissive cell types. However, the achieved results being implemented in specific mouse strains and other small-animal models cannot always be extrapolated to that of other species and modification of the AAV capsid may lead to unpredicted structural and tropism changes. Thus, further exploration of safer and more effective strategies to improve AAV transduction at a lower vector dose, especially in a manner that induces consistent transgene expression without limitation of species and alteration of tissue tropism, is still of critical clinical importance.

The present invention overcomes shortcomings in the art by providing novel methods and compositions for increasing transduction efficiency.

SUMMARY OF THE INVENTION

The present invention is based on the discovery that cell membrane fusion proteins can enhance introduction (e.g., transduction) of a heterologous agent into a host cell. Accordingly, one aspect of the present invention relates to methods of introducing a heterologous agent into a host cell, comprising contacting the host cell with the heterologous agent in the presence of a cell membrane fusion protein or a functional fragment or derivative thereof. In some embodiments, such methods may further comprise combining the cell membrane fusion protein or functional fragment or derivative thereof and the heterologous agent; optionally, incubating the combined cell membrane fusion protein or functional fragment or derivative thereof and the heterologous agent; and contacting the host cell using the combined cell membrane fusion protein or functional fragment or derivative thereof and the heterologous agent. Additionally, in some embodiments, the methods further comprise forming a complex between the cell membrane fusion protein or functional fragment or derivative thereof and the heterologous agent; and then contacting the host cell with the complex.

A further aspect of the invention relates to compositions for introducing a heterologous agent into a host cell, wherein the compositions comprise (a) a heterologous agent encoding a polypeptide or functional nucleic acid, and (b) an effective amount of a cell membrane fusion protein or a functional fragment or derivative thereof.

An additional aspect of the invention relates to methods of expressing a polypeptide or functional nucleic acid in a subject, comprising administering to the subject a composition according to an embodiment of the invention and expressing the polypeptide or functional nucleic acid in the subject.

Another aspect of the invention relates to methods of editing a gene in a subject, comprising administering to the subject a composition according to an embodiment of the invention, and expressing the polypeptide or functional nucleic acid in the subject, thereby editing a gene in the subject.

A further aspect of the invention relates to methods of treating a disorder in a subject in need thereof, comprising administering to the subject a composition according to an embodiment of the invention, and expressing the polypeptide or functional nucleic acid in the subject, thereby treating a disorder in the subject.

In the methods and compositions described herein, any heterologous agent may be used, but in some embodiments, the heterologous is a nucleic acid delivery vector, such as a viral vector. In particular embodiments, the heterologous agent is a recombinant AAV vector. In the methods and compositions described herein, any suitable cell membrane fusion protein may be used herein. However, in some cases, the cell membrane fusion protein is a fragment of a ferlin protein, and in particular embodiments, the cell membrane fusion protein is an isolated FerA domain fragment. Additionally, in particular embodiments, at least two different types of FerA domain proteins or functional fragments or derivatives thereof are used.

These and other aspects of the invention are set forth in more detail in the description of the invention below.

BRIEF DESCRIPTION OF THE DRAWINGS

FIGS. 1A-1B show that mouse otoferlin FerA domain increased AAV transduction in vivo via systemic administration. $5 \times 10^{10}$ vg of AAV9/luc alone or the complex of AAV9/luc incubated with mOto-FerA at multiple molecule ratios (1:0, 1:200, 1:2000, 1:20,000, and 1:200,000 equal to 0 μg, 0.005 μg, 0.05 μg, 0.5 μg, and 5 μg, respectively) were administered via intravenous injection. Luminescence imaging was performed (FIG. 1A) and the photon signal was measured and calculated (FIG. 1B) on day 1 and day 3. The data of each group represent the average and SD from five mice. *$p<0.001$, $p<0.01$, and *$p<0.05$ compared to control mice with AAV9/luc treatment only.

(FIG. 2A) Images were taken for luminescence analysis on days 3, 9, and 14 following retro-orbital injections of female C57BL/6 mice. (FIG. 2B) The average luciferase signal for liver and brain was calculated. (FIG. 2C) The luciferase expression and (FIG. 2D) gene copy numbers in heart, liver, kidney, brain, and muscle were determined separately. The data of each group represent the average and SD from five mice. *$p<0.001$, $p<0.01$, and *$p<0.05$ compared to control mice with AAV9/luc treatment only.

FIGS. 3A-3D show mouse otoferlin FerA enhanced the transduction of AAV6 and AAV8 in vivo by systemic injection. $1 \times 10^{10}$ vg of AAV6/luc or AAV8/luc with or without pre-incubation of mOto-FerA were injected into 5-6-week-old female C57BL/6 mice via retro-orbital injection. Imaging was carried out (FIG. 3A and FIG. 3B) and photon signal was calculated (FIG. 3C and FIG. 3D) at day 3, 7, and 14 after vector administration. The data of each group represent the average and SD from five mice. **$p<0.01$ and *$p<0.05$ compared to control mice with AAV/luc treatment only.

FIGS. 4A-4I show mouse otoferlin FerA increased muscle transduction of AAV. $2 \times 10^9$ vg of AAV9/luc, AAV8/luc, or AAV6/luc particles were first incubated with 1 μg mOto-FerA for 2 h at 4° C., then administered via intramuscular injection in the left legs (face-up) in 6-week-old female C57BL/6 mice (n=5). As the internal control, AAV vectors only were injected into the right legs (face-up). Several weeks (W1, W2, and W3) post AAV application, in vivo luminescence imaging was performed (FIGS. 4A, 4D, and 4G). The photon signal (FIGS. 4B, 4E, and 4H) and gene copy numbers (FIGS. 4C, 4F, and 4I) in the leg muscle were measured and calculated. The data of each group represent the average and SD from five mice. *$p<0.001$, $p<0.01$, and *$p<0.05$ compared to control mice with AAV/luc treatment only. R: right leg, L: left leg.

(FIG. 6A) Total expressed hFIX protein in mouse plasma was determined by an ELISA assay. (FIG. 6B) Circulating functional hFIX activity was determined by an in vitro aPTT assay. The data of each group represent the average and SD from five mice. *$p<0.001$, $p<0.01$, and *$p<0.05$ compared to control mice with scAAV8/hFIX treatment only.

FIGS. 7A-7E show FerA domains directly interacting with AAV9. Purified AAV9 was first incubated with hDys-FerA (FIG. 7A), hMyo-FerA (FIG. 7B), hOto-FerA (FIG. 7C), or mOto-FerA domain (FIG. 7D) for 2 h at 4° C., then CaptureSelect™ biotin anti-AAV9 conjugate was added into the complex for another 1 h at RT, followed by Streptavidin C1 beads-based pull down assays and immunoblotting analysis with indicated ferlin antibodies. Meanwhile, the incubated complexes of AAV9 with Streptavidin C1 beads, Streptavidin C1 beads with FerA domains, AAV9 and FerA domains with C1 beads, and the biotin anti-AAV9 conjugate and FerA domains with C1 beads were separately included as controls. sc: streptavidin C1 beads, 9: AAV9, B: biotin anti-AAV9 conjugate, hDF: hDys-FerA, hMF: hMyo-FerA, hOF: hOto-FerA, mOF: mOto-FerA. IB: immunoblot. (FIG. 7E) Immunoblot using B1 and dysferlin antibodies of pull down assay in which biotin-GFP-hDys-FerA protein was incubated with AAV9, followed by addition of Streptavidin C1 beads for 0.5 h at RT. IB: immunoblot.

(FIG. 9A) hCMEC/D3 cells were cultured in a monolayer and incubated with either AAV9 or AAV9-hDys-FerA complex. The medium in the basal chamber was collected at different indicated time points and the virus genome copy number was determined by qPCR. At the same time, a permeability assay for dextran conjugated with FITC (FITC-dextran) was also performed to check membrane integrity (FIG. 9B). In brief, at the indicated time points, FITC-dextran was added to the cells seeded on the collagen-coated cell inserts and incubated at RT for 0.5 h. Following incubation, inserts were removed and the medium remaining in the basal chamber was collected and analyzed for FITC-dextran fluorescence intensity using a microplate reader (BioTek Instruments Inc., Winooski, VT) with excitation and emission wavelengths of 485 nm and 530 nm. All treatments were performed in triplicate. ns $p > 0.05$, ***$p < 0.001$ and *$p < 0.05$ compared to cells with AAV9/luc treatment only.

(FIG. 10A) Mice were administered the incubated complex of $1 \times 10^{11}$ vg AAV9/luc and 5 µg hDys-FerA via retro-orbital injection. Luciferase expression was measured on days 1, 3, 7, and 14. (FIG. 10B) Blood was also collected from the retro-orbital plexus at different time points (5 min, 2 h, 24 h, and 48 h) after injection, and the viral titers were tested by qPCR. The data represent the average and SD from five mice. *$p < 0.05$ and **$p < 0.01$ compared to the AAV9/luc alone treatment group.

FIGS. 11A-11F show mouse otoferlin FerA domain increased AAV transduction in vitro. (FIG. 11A) Complexes of pre-incubated AAV9 and mOto-FerA domain at different molecule ratios (1:0, 1:20, 1:200, 1:2000, 1:20,000, and 1:200,000) were added into the Huh7 cells for 48 h, and then the cytotoxicity was measured using the MTT assay. (FIG. 11B) AAV9/luc vectors ($1 \times 10^4$ vg/cell) pre-incubated with or without mOto-FerA at various molecule ratios (1:0, 1:20, 1:200, 1:2000, 1:20,000, and 1:200,000) were transduced into Huh7 cells. The transduction efficiency of different groups was tested after 48 h. Next, the transduction of AAV/luc vectors from AAV6, AAV8, and AAV9 ($1 \times 10^4$ vg/cell) pre-incubated with FerA at the molecule ratios of 1:20,000 and 1:200,000 were tested in the Huh7 (FIG. 11C), hCMEC/D3 (FIG. 11D), HeLa (FIG. 11E), and C2C12 (FIG. 11F) cell lines. The relative fold of luciferase value compared to AAV/luc treatment only was calculated and shown. ns $p > 0.05$, *$p < 0.05$, and **$p < 0.01$ compared to the AAV/luc alone group transduction. The data represent the average and SD from at least triplicate experiments.

FIGS. 12A-12D show multiple human FerA domains enhanced AAV9 transduction in vitro. (FIG. 12A) The cytotoxicity of different concentrations (0.05 µg and 0.5 µg) of human FerA domains (hOto-, hDys-, and hMyo-derived) was evaluated using the MTT assay. Next, multiple human FerA domains (hDys-/hMyo-/hOto-FerA) with different concentrations (0.05 µg and 0.5 µg) were incubated with $1 \times 10^9$ vg AAV9 for 2 h at 4° C. and added into Huh7 (FIG. 12B), HeLa (FIG. 12C), and hCMEC/D3 (FIG. 12D) cell lines. After 48 h, cells were lysed with passive lysis buffer and luciferase activity of different groups was measured. ns $p > 0.05$ and *$p < 0.05$ compared to AAV9/luc transduction group only. The data represent the average and SD from at least triplicate experiments.

FIGS. 14A-14C show that FerA did not cause liver cytotoxicity. Liver enzyme values of serum alanine transaminase (ALT) (FIG. 13A) and aspartate transaminase (AST) (FIG. 13B) were monitored at different time points (2 h, day 1 and 7) post administration with commercial reagent kits. The data represent the average and SD from five mice. (FIG. 13C) Representative pictures of liver tissue sections stained by H&E at different objectives. Scale bars, 200 µm (Objective 4×optical axis for I and II) and 50 µm (Objective 20×optical axis for III and IV).

Figure 2A:
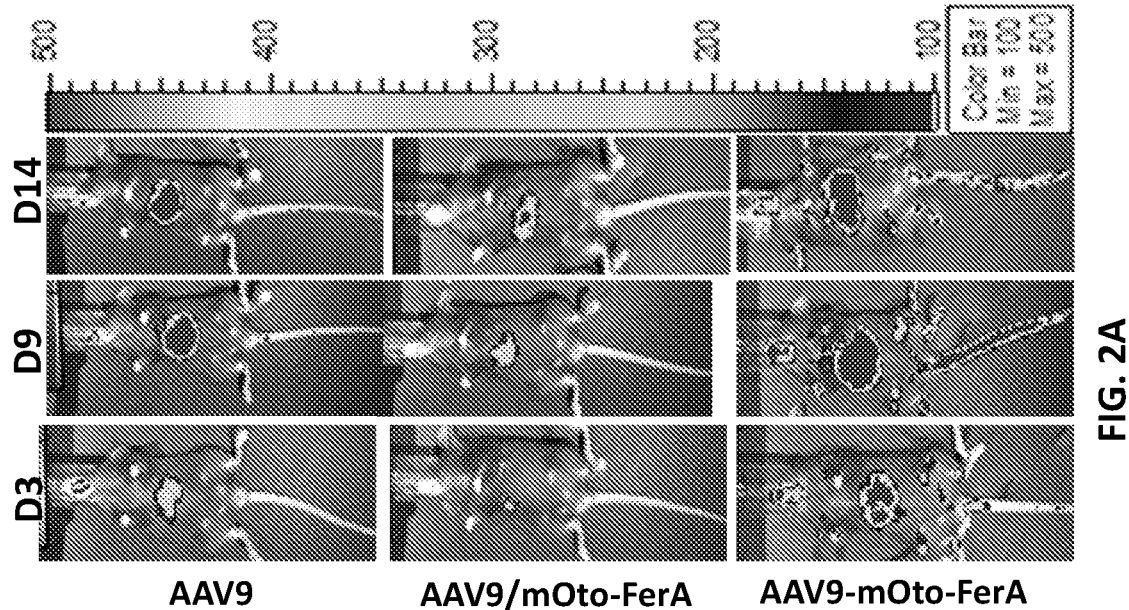
FIGS. 2A-2D show direct interaction of mouse otoferlin FerA with AAV9 in enhanced transduction in vivo via systemic administration. Three groups were designed as below: $1 \times 10^{10}$ vg AAV9 only (AAV9 cohort), AAV9 vectors and mOto-FerA injected simultaneously without pre-incubation (AAV9/mOto-FerA cohort), and AAV9 vectors pre-incubated with 5 μg mOto-FerA for 2 h at 4° C. (AAV9-mOto-FerA cohort).

Note: In these figures, *, , and * were used to denote $p < 0.05$, $p < 0.01$, and $p < 0.001$, respectively and were considered statistically significant. Graphs are representative of data sets from at least three independent assays.

DETAILED DESCRIPTION OF EMBODIMENTS OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

General Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together.

The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "tropism" as used herein refers to preferential but not necessarily exclusive entry of the vector (e.g., virus vector) into certain cell or tissue type(s) and/or preferential but not necessarily exclusive interaction with the cell surface that facilitates entry into certain cell or tissue types, optionally and preferably followed by expression (e.g., transcription and, optionally, translation) of sequences carried by the vector contents (e.g., viral genome) in the cell, e.g., for a recombinant virus, expression of the heterologous nucleotide sequence(s).

The term "tropism profile" refers to the pattern of transduction of one or more target cells, tissues and/or organs. Representative examples of chimeric AAV capsids have a tropism profile characterized by efficient transduction of cells of the central nervous system (CNS) with only low transduction of peripheral organs (see e.g. U.S. Pat. No. 9,636,370 McCown et al., and US patent publication 2017/

0360960 Gray et al.). Vectors (e.g., virus vectors, e.g., AAV capsids) expressing specific tropism profiles may be referred to as "tropic" for their tropism profile, e.g., neuro-tropic, liver-tropic, etc.

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide," "nucleic acid," or "nucleotide sequence" may be of RNA, DNA or DNA-RNA hybrid sequences (including both naturally occurring and non-naturally occurring nucleotides), but is preferably either a single or double stranded DNA sequence.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. The region in a nucleic acid sequence or polynucleotide in which one or more regulatory elements are found may be referred to as a "regulatory region."

As used herein with respect to nucleic acids, the term "operably linked" refers to a functional linkage between two or more nucleic acids. For example, a promoter sequence may be described as being "operably linked" to a heterologous nucleic acid sequence because the promoter sequences initiates and/or mediates transcription of the heterologous nucleic acid sequence. In some embodiments, the operably linked nucleic acid sequences are contiguous and/or are in the same reading frame.

The term "open reading frame (ORF)," as used herein, refers to the portion of a polynucleotide (e.g., a gene) that encodes a polypeptide, and is inclusive of the initiation start site (i.e., Kozak sequence) that initiates transcription of the polypeptide. The term "coding region" may be used interchangeably with open reading frame.

The term "codon-optimized," as used herein, refers to a gene coding sequence that has been optimized to increase expression by substituting one or more codons normally present in a coding sequence with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry and/or initiation sites, such as Kozak sequences. Desirably, a codon-optimized gene exhibits improved protein expression, for example, the protein encoded thereby is expressed at a detectably greater level in a cell compared with the level of expression of the protein provided by the wildtype gene in an otherwise similar cell. Codon-optimization also provides the ability to distinguish a codon-optimized gene and/or corresponding mRNA from an endogenous gene and/or corresponding mRNA in vitro or in vivo.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the term "modified," as applied to a polynucleotide or polypeptide sequence, refers to a sequence that differs from a wildtype sequence due to one or more deletions, additions, substitutions, or any combination thereof.

As used herein, by "isolate" (or grammatical equivalents) a virus vector, it is meant that the virus vector is at least partially separated from at least some of the other components in the starting material.

By the term "treat," "treating," or "treatment of" (or grammatically equivalent terms) is meant to reduce or to at least partially improve or ameliorate the severity of the subject's condition and/or to alleviate, mitigate or decrease in at least one clinical symptom and/or to delay the progression of the condition.

As used herein, the term "prevent," "prevents," or "prevention" (and grammatical equivalents thereof) means to delay or inhibit the onset of a disease. The terms are not meant to require complete abolition of disease, and encompass any type of prophylactic treatment to reduce the incidence of the condition or delays the onset of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

A "heterologous nucleotide sequence" or "heterologous nucleic acid," with respect to a virus, is a sequence or nucleic acid, respectively, that is not naturally occurring in the virus. Generally, the heterologous nucleic acid or nucleotide sequence comprises an open reading frame that encodes a polypeptide and/or a nontranslated RNA.

A "vector" refers to a compound, composition, or construct used as a vehicle to carry or deliver foreign or exogenous genetic material into a target cell, where it can be replicated and/or expressed. A vector containing foreign or heterologous or exogenous nucleic acid is termed a recombinant vector. Examples of nucleic acid vectors are plasmids, viral vectors, cosmids, expression cassettes, and artificial chromosomes. Recombinant vectors typically contain an origin of replication, a multicloning site, and a selectable marker. The nucleic acid sequence typically consists of an insert (recombinant nucleic acid or transgene) and a nucleic acid sequence that serves as the "backbone" of the vector. The purpose of a vector which transfers genetic material to a target cell is typically to isolate, multiply, or express the insert in the target cell. Expression vectors (expression constructs or expression cassettes) are for the expression of the exogenous gene in the target cell, and generally have a promoter sequence that drives expression of the exogenous gene/ORF. Insertion or introduction of a vector into the target cell is referred to as transformation or transfection for bacterial and eukaryotic cells, although insertion of a viral vector is often called transduction. The term "vector" may also be used in general to describe items that serve to carry foreign or heterologous or exogenous genetic material into a target cell, such as, but not limited to, a transformed cell or a nanoparticle.

As used herein, the term "viral vector" and "delivery vector" (and similar terms) in a specific embodiment generally refers to a virus particle that functions as a nucleic acid delivery vehicle, and which comprises the viral nucleic acid (i.e., some or all of the vector genome) packaged within the virus particle. Viral vectors according to the present invention may include chimeric AAV capsids according to the invention and can package an AAV or rAAV genome or any other nucleic acid including viral nucleic acids. Alternatively, in some contexts, the terms "viral vector" and "delivery vector" (and similar terms) may be used to refer to the vector genome (e.g., vDNA) in the absence of the virion and/or to a viral capsid or virus like particle (VLP) that acts as a transporter to deliver molecules tethered to the capsid or VLP and/or packaged within the capsid or VLP.

As used herein, the term "amino acid" encompasses any naturally occurring amino acids, modified forms thereof, and synthetic amino acids, including non-naturally occurring amino acids.

Naturally occurring, levorotatory (L-) amino acids are shown in Table 1.

TABLE 1

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 2) or can be an amino acid that is modified by post-translation modification (e.g., acetylation, amidation, formylation, hydroxylation, methylation, phosphorylation or sulfatation).

TABLE 2

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |

13

TABLE 2-continued

| Amino Acid Residue Derivatives | |
| --- | --- |
| Modified Amino Acid Residue | Abbreviation |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) *Annu. Rev. Biophys. Biomol. Struct.* 35:225-49. These unnatural amino acids can advantageously be used to chemically link molecules of interest to the AAV capsid protein.

A "functional fragment" of a polypeptide or protein, as used herein, means a portion of a larger polypeptide that substantially retains its ability to enhance or increase transduction efficiency. For example, an isolated FerA domain polypeptide is a functional fragment of the larger ferlin protein.

As used herein, the term "derivative" is used to refer to a polypeptide which differs from a naturally occurring protein or a functional fragment by minor modifications to the naturally occurring polypeptide, but which substantially retains the biological activity of the naturally occurring protein. Minor modifications include, without limitation, changes in one or a few amino acid side chains, changes to one or a few amino acids (including deletions, insertions, and/or substitutions) (e.g., less than about 20, 15, 10, 9, 8, 7, 6, 5, 4, 3, or 2 changes), changes in stereochemistry of one or a few atoms (e.g., D-amino acids), and minor derivatizations, including, without limitation, methylation, glycosylation, phosphorylation, acetylation, myristoylation, prenylation, palmitation, amidation, and addition of glycosylphosphatidyl inositol.

The term "substantially retains," as used herein, refers to al fragment, derivative, or other variant of a polypeptide that retains at least about 50% of the activity of the naturally occurring polypeptide (e.g., binding to an antibody), e.g., about 60%, 70%, 80%, 90% or more.

The term "template" or "substrate" is used herein to refer to a polynucleotide sequence that may be replicated to produce the viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

Methods of Introducing Heterologous Agents into Host Cells

One aspect of the present invention relates to methods of introducing a heterologous agent into a host cell, comprising contacting the host cell with the heterologous agent in the presence of a cell membrane fusion protein or a functional fragment or derivative thereof.

Another aspect relates to methods of expressing a polypeptide or functional nucleic acid in a subject, comprising administering to the subject a composition comprising (a) a heterologous agent encoding a polypeptide or functional nucleic acid, and (b) an effective amount of a cell membrane fusion protein or a functional fragment or derivative thereof, and expressing the polypeptide or functional nucleic acid in the subject.

A further aspect of the invention relates to methods of editing a gene in a subject, comprising administering to the subject a composition comprising (a) a heterologous agent encoding a polypeptide or functional nucleic acid, and (b) an effective amount of a cell membrane fusion protein or a functional fragment or derivative thereof, and expressing the polypeptide or functional nucleic acid in the subject, thereby editing a gene in the subject.

An additional aspect of the invention relates to methods of treating a disorder in a subject in need thereof, comprising administering to the subject a composition comprising (a) a heterologous agent encoding a polypeptide or functional nucleic acid, and (b) an effective amount of a cell membrane fusion protein or a functional fragment or derivative thereof, and expressing the polypeptide or functional nucleic acid in the subject, thereby treating a disorder in the subject.

Heterologous Agents

As used herein, the term "heterologous agent" refers to an agent that is not naturally found in the subject to which the agent is to be administered. The heterologous agent may be one for which neutralizing antibodies are present in the subject prior to administration of the heterologous agent or one that is likely to raise neutralizing antibodies upon administration to the subject. The heterologous agent may be one that has never been administered to the subject. The heterologous agent may be one that has previously been administered to the subject.

In some embodiments, the heterologous agent may be a nucleic acid delivery vector, e.g., a viral vector or a non-viral vector. In some embodiments, the viral vector is an adeno-associated virus, retrovirus, lentivirus, poxvirus, alphavirus, baculovirus, vaccinia virus, herpes virus, Epstein-Barr virus, or adenovirus vector. In some embodiments, the non-viral vector is a plasmid, liposome, electrically charged lipid, nucleic acid-protein complex, or biopolymer. In some embodiments, the heterologous agent is a gene editing complex, e.g., a CRISPR complex.

In some embodiments of the invention, the heterologous agent is a parvovirus vector. The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

In some embodiments of the invention, the heterologous agent is a parvovirus within the genus Dependovirus. The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 3. A number of additional AAV serotypes and clades have been identified (see, e.g., Gao et al., (2004) J. Virol. 78:6381-6388 and Table 3), which are also encompassed by the term "AAV."

As discussed above, the parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73:939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) Virol. 33-: 375-383; Mori et al., (2004) *Virol.* 330:375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 3. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

The term "AAV viral vectors" includes "chimeric" AAV nucleic acid capsid coding sequence or AAV capsid protein is one that combines portions of two or more capsid sequences. A "chimeric" AAV virion or particle comprises a chimeric AAV capsid protein.

TABLE 3

| AAV Serotypes/Isolates | GenBank Accession Number |
| --- | --- |
| Clonal Isolates | |
| Avian AAV ATCC VR-865 | AY186198, AY629583, NC_004828 |
| Avian AAV strain DA-1 | NC_006263, AY629583 |
| Bovine AAV | NC_005889, AY388617 |
| AAV4 | NC_001829 |
| AAV5 | AY18065, AF085716 |
| Rh34 | AY243001 |
| Rh33 | AY243002 |
| Rh32 | AY243003 |
| AAV10 | AY631965 |
| AAV11 | AY631966 |
| AAV12 | DQ813647 |
| AAV13 | EU285562 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |

TABLE 3-continued

| AAV Serotypes/Isolates | GenBank Accession Number |
| --- | --- |
| Clade B | |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |

TABLE 3-continued

| AAV Serotypes/Isolates | GenBank Accession Number |
| --- | --- |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| | |
| AAV9 (Hu14) | AY530579 |
| Hu31 | AY530596 |
| Hu32 | AY530597 |

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged. The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

The AAV viral vectors of the invention may include a recombinant AAV vector genome. A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end. The terms "rAAV particle" and "rAAV virion" are used interchangeably here. A "rAAV particle" or "rAAV virion" comprises a rAAV vector genome packaged within an AAV capsid.

The term "terminal repeat" or "TR" includes any viral terminal repeat or synthetic sequence that forms a hairpin structure and functions as an inverted terminal repeat (ITR)

(i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 3). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

Further, the viral capsid or genomic elements can contain other modifications, including insertions, deletions and/or substitutions.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wildtype or synthetic. A wildtype large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 3). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) Human Gene Therapy 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

In some embodiments, the heterologous agent encodes a protein or nucleic acid. In some embodiments, the protein is an enzyme, a regulatory protein, or a structural protein, e.g., one that can substitute for a missing or defective protein in a subject. In some embodiments, the nucleic acid is a functional nucleic acid, e.g., an antisense nucleic acid or an inhibitory RNA.

Any nucleic acid sequence(s) of interest may be delivered in the nucleic acid delivery vectors of the present invention. Nucleic acids of interest include nucleic acids encoding polypeptides, including therapeutic (e.g., for medical or veterinary uses), immunogenic (e.g., for vaccines), or diagnostic polypeptides.

Therapeutic polypeptides include, but are not limited to, cystic fibrosis transmembrane regulator protein (CFTR), dystrophin (including mini- and micro-dystrophins (see, e.g, Vincent et al., (1993) Nature Genetics 5:130; U.S. Patent Publication No. 2003/017131; International publication WO/2008/088895, Wang et al., Proc. Natl. Acad. Sci. USA 97:13714-13719 (2000); and Gregorevic et al., Mol. Ther. 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) Nature 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor α soluble receptor), S100A1, parvalbumin, adenylyl cyclase type 6, a molecule that effects G-protein coupled receptor kinase type 2 knockdown such as a truncated constitutively active bARKct, anti-inflammatory factors such as IRAP, anti-myostatin proteins, aspartoacylase, and monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. Parvovirus vectors can also be used to deliver monoclonal antibodies and antibody fragments, for example, an antibody or antibody fragment directed against myostatin (see, e.g., Fang et al., Nature Biotechnol. 23:584-590 (2005)).

Nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the nucleic acid may encode a functional nucleic acid, i.e., nucleic acid that functions without getting translated into a protein, e.g., an antisense nucleic acid, a ribozyme (e.g., as described in U.S. Pat. No. 5,877,022), RNAs that effect spliceosome-mediated trans-splicing (see, Puttaraju et al., (1999) Nature Biotech. 17:246; U.S. Pat. Nos. 6,013,487; 6,083,702), interfering RNAs (RNAi) including siRNA, shRNA or miRNA that mediate gene silencing (see, Sharp et al., (2000) Science 287:2431), and other non-translated RNAs, such as "guide" RNAs (Gorman et al., (1998) Proc. Nat. Acad. Sci. USA 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., J. Gene Med. 10:132-142 (2008) and Li et al., Acta Pharmacol Sin. 26:51-55 (2005)); phospholamban inhibitory or dominant-negative molecules such as phospholamban S16E (e.g., to treat cardiovascular disease, see, e.g., Hoshijima et al. Nat. Med. 8:864-871 (2002)), RNAi to adenosine kinase (e.g., for epilepsy), RNAi to a sarcoglycan [e.g., α, β, γ], RNAi against myostatin, myostatin propeptide, follistatin, or activin type II soluble receptor, RNAi against anti-inflammatory polypeptides such as the Ikappa B dominant mutant, and RNAi directed against pathogenic organisms and viruses (e.g., hepatitis B virus, human immunodeficiency virus, CMV, herpes simplex virus, human papilloma virus, etc.).

Alternatively, in particular embodiments of this invention, the nucleic acid may encode protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, enos, inos, or bone morphogenic proteins (including BNP 2, 7, etc., RANKL and/or VEGF).

The nucleic acid delivery vectors may also comprise a nucleic acid that shares homology with and recombines with a locus on a host chromosome. This approach can be utilized, for example, to correct a genetic defect in the host cell.

The present invention also provides nucleic acid delivery vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882, 652, 5,863,541 to Samulski et al.). The antigen may be presented in the parvovirus capsid. Alternatively, the antigen may be expressed from a nucleic acid introduced into a recombinant vector genome. Any immunogen of interest as described herein and/or as is known in the art can be provided by the nucleic acid delivery vectors.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

It will be understood by those skilled in the art that the nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

Cell Membrane Fusion Proteins

As used herein, the term "cell membrane fusion protein" refers to any polypeptide that causes or enhances fusion of biological membranes. In some embodiments, the cell membrane fusion protein is a transmembrane protein or a functional fragment or derivative thereof, and in particular embodiments, is a type II transmembrane protein or a functional fragment or derivative thereof.

In some embodiments, the transmembrane protein is a ferlin protein or a functional fragment or derivative thereof. Ferlin proteins include multiple tandem C2 domains (Ca2+ regulated, phospholipid-binding domains), a centrally positioned FerA domain and anchored by a C-terminal transmembrane protein. In some embodiments, the ferlin protein is a FerA functional fragment or a derivative thereof of a ferlin protein. In particular embodiments, the FerA fragment is an isolated FerA functional fragment. Any suitable FerA domain could be used in the methods and compositions described herein but in some cases, the FerA domain fragments are from the following ferlin proteins: dysferlin (Fer1L1), otoferlin (Fer1L2), and myoferlin (Fer1L3), Fer1L4, Fer1L5, and Fer1L6. The ferlin protein/FerA domain may be from any suitable organism, but in particular embodiments, is from a mammal, such as a mouse, cat, dog, rat, chimpanzee, or human. In particular embodiments, the isolated FerA domain is a fragment from human dysferlin (residues 670-783) [GenBank AAC63519.1], human myoferlin (residues 610-723) [GenBank AAF27177.1], or human otoferlin (residues 723-839) [Swiss-Prot Q9HC10.3].

In some embodiments, the cell membrane fusion protein is a derivative of a cell membrane fusion protein described herein. In some embodiments, the derivative of a cell membrane fusion protein or cell membrane fusion protein functional fragment contains mutations (deletions, insertions, and/or substitutions in any combination) of 10 or fewer amino acid residues, e.g., 10, 9, 8, 7, 6, 5, 4, 3, or 2 or fewer mutations. In some embodiments, the cell membrane fusion protein derivative comprises an amino acid sequence that is at least about 80%, 85%, 90%, 91%, 92%, 93%, 94%, 95%, 96%, 97%, 98%, or 99% identical to Fer1L1, Fer1L2, Fer1L3, Fer1L4, Fer1L5 or Fer1L6, or any other FerA domain, now known or later discovered, from a ferlin protein.

In some embodiments, the cell membrane fusion protein or a functional fragment or derivative thereof can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases. Such blocking agents can include, without limitation, additional related or unrelated amino acids (e.g., one or more D-amino acids) or peptide sequences that can be attached to the amino and/or carboxyl terminal residues of the protein to be administered. This can be done either chemically during the synthesis of the protein or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the proteins can be covalently or noncovalently coupled to pharmaceutically acceptable "carrier" proteins prior to administration.

The cell membrane fusion protein or a functional fragment or derivative thereof can be produced by any suitable method. In some embodiments, the cell membrane fusion protein or a functional fragment or derivative thereof is produced recombinantly using methods well known in the art and as described herein.

Introduction into Host Cells

As used herein, "transduction" of a cell by a virus vector (e.g., an AAV vector) means entry of the virus vector into the cell and transfer of nucleic acid into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control). Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the CNS or tissues other than muscle, e.g., liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., CNS cells or muscle cells).

Those skilled in the art will appreciate that transcription of a heterologous nucleic acid sequence from a viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

Any suitable amount of the cell membrane fusion protein may be used to increase efficiency of the introduction (e.g., transduction) of the heterologous agent into the host cell. In some embodiments, a treatment effective amount of the cell membrane fusion protein is an amount of cell membrane fusion protein that increases or enhances introduction (e.g., transduction) efficiency of a heterologous agent into a host cell relative to a negative control. Any increase in introduction efficiency may be beneficial, but in some embodiments, the cell membrane fusion protein or a functional fragment or derivative thereof increases the efficiency of the introduction relative to a negative control by at least 110%, 120%, 150%, 200%, 300%, 400%, 500%, or 1000%.

Any suitable ratio between the heterologous agent and cell membrane fusion protein may be used. However, in some embodiments, the cell membrane fusion protein, or functional fragment or derivative thereof, and the heterologous agent are combined at a molecular ratio of at least about 200:1 cell membrane fusion protein to heterologous agent, e.g., at least about 500:1, 1,000:1, 2,000:1, 5,000:1, 10,000:1, 15,000:1, 20,000:1, 30,000:1, 40,000:1, 50,000:1, 75,000:1, 100,000:1, 150,000:1, 200,000:1 or any range therein. In some embodiments, the cell membrane fusion protein or functional fragment or derivative thereof and the heterologous agent are combined at a molecular ratio of less than about 200:1 cell membrane fusion protein to heterologous agent, e.g., less than about 500:1, 1,000:1, 2,000:1, 5,000:1, 10,000:1, 15,000:1, 20,000:1, 30,000:1, 40,000:1, 50,000:1, 75,000:1, 100,000:1, 150,000:1, 200,000:1 or any range therein. Furthermore, in some embodiments, the cell membrane fusion protein or functional fragment or derivative thereof and the heterologous agent are combined at a molecular ratio in a range of about 20,000:1 to about 200,000:1 cell membrane fusion protein to heterologous agent. In some embodiments, an AAV viral vector is combined with a FerA domain fragment at a molecular ratio of at least 20,000:1, and in some embodiments in a range of about 20,000:1 to about 200,000:1 FerA domain fragment to AAV viral particle.

The cell membrane fusion protein, or fragment or derivative thereof, may be administered to the subject by any schedule found to be effective to increase introduction (e.g., transduction) efficiency of the heterologous agent into the host cell. In some embodiments, the heterologous agent is combined with the cell membrane fusion protein or a functional fragment or derivative thereof prior to administration to the subject, e.g., the two components are mixed together prior to administration in a single composition. In some cases, the heterologous agent and the cell membrane fusion protein or a functional fragment or derivative thereof may be incubated for a period of time before introduction. For example, the heterologous agent and the cell membrane fusion protein or a functional fragment or derivative thereof may be incubated for 1, 2, 3, 4, 5, 8, 12, 24 hours or more. The heterologous agent and the cell membrane fusion protein or a functional fragment or derivative thereof may be incubated at any suitable temperature, and in some cases, these components will be incubated at a time and temperature that allows for the heterologous agent and the cell membrane fusion protein or a functional fragment or derivative thereof to associate and form a complex. In some cases, the heterologous agent and the cell membrane fusion protein may be incubated at a temperature below about 10° C., and in some case below about 5° C. In some embodiments, the heterologous agent and cell membrane fusion protein are incubated together, optionally in a pharmaceutically acceptable carrier, at a temperature less than about 5° C. for at least 1, 2, 3, 4, or 5 hours.

The heterologous agent may be combined with the cell membrane fusion protein or a functional fragment or derivative thereof in any suitable liquid carrier, e.g., water, buffer, or saline, e.g., phosphate-buffered saline. In some embodiments, the liquid carrier is physiologically compatible, e.g., suitable for administration to a subject.

In other embodiments of the invention, the cell membrane fusion protein or a functional fragment or derivative thereof and the heterologous agent are administered in separate compositions. In some embodiments, the cell membrane fusion protein or a functional fragment or derivative thereof is administered to the subject prior to administration of the heterologous agent, e.g., at least about 1, 5, 10, 15, 20, 30, 40, or 50 minutes or at least about 1, 2, 3, 4, 5, 6, 12, 18, or 24 hours prior to administration of the heterologous agent. In some embodiments, the cell membrane fusion protein or a functional fragment or derivative thereof is administered to the subject concurrently with administration of the heterologous agent. As used herein, the term "concurrently" means sufficiently close in time to produce a combined effect (that is, concurrently can be simultaneously, or it can be two or more events occurring within a short time period before or after each other).

The cell(s) into which the heterologous agent, e.g., a nucleic acid delivery vector, is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), blood vessel cells (e.g., endothelial cells, intimal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, kidney cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above. Furthermore, the cells may be dividing or nondividing.

Embodiments of the invention may be performed in vitro or in vivo. One aspect of the present invention is a method of transferring a heterologous agent to a cell in vitro, e.g., for research purposes or as part of an ex vivo method. The heterologous agent (e.g., nucleic acid delivery vector/viral vector), along with the cell membrane fusion protein, may be introduced into the cells at the appropriate amount, e.g., multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

In particular embodiments, the cells have been removed from a subject, the nucleic acid delivery vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the nucleic acid delivery vectors can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells with the nucleic acid delivery vector introduced are administered to the subject in a treatment effective or prevention effective amount in combination with a pharmaceutical carrier.

The nucleic acid delivery vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The nucleic acid delivery vectors can also be used to produce a polypeptide of interest or functional RNA in a subject (e.g., using the subject as a bioreactor to produce the polypeptide or to observe the effects of the functional nucleic acid on the subject, for example, in connection with screening methods). The nucleic acid delivery vectors may also be employed to provide a functional nucleic acid to a cell in vitro or in vivo. Expression of the functional nucleic acid in the cell, for example, can diminish expression of a particular target protein by the cell. Accordingly, functional nucleic acid can be administered to decrease expression of a particular protein in a subject in need thereof.

Nucleic acid delivery vectors also find use in diagnostic and screening methods, whereby a nucleic acid of interest is transiently or stably expressed in a transgenic animal model.

The nucleic acid delivery vectors can also be used for various non-therapeutic purposes, including but not limited to use in protocols to assess gene targeting, clearance, transcription, translation, etc., as would be apparent to one skilled in the art. The nucleic acid delivery vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Pharmaceutical Formulations, Subjects, and Modes of Administration

Provided according to embodiments of the invention are compositions that include a heterologous agent and a cell membrane fusion protein or a functional fragment or derivative thereof. Also provided herein are pharmaceutical compositions comprising a heterologous agent and cell membrane fusion protein or a functional fragment or derivative thereof in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form. The present invention also provides a complex between the heterologous agent and the cell membrane fusion protein in a pharmaceutically acceptable carrier and, optionally, other medicinal agents, pharmaceutical agents, stabilizing agents, buffers, carriers, adjuvants, diluents, etc. By "pharmaceutically acceptable" it is meant a material that is not toxic or otherwise undesirable, i.e., the material may be administered to a subject without causing any undesirable biological effects.

A further aspect of the invention is a method of administering the heterologous agent (e.g., nucleic acid delivery vector) and the cell membrane fusion protein or a functional fragment or derivative to subjects. Administration of the nucleic acid delivery vectors to a human subject or an animal in need thereof can be by any means known in the art. Optionally, the nucleic acid delivery vector is delivered in a treatment effective or prevention effective dose in a pharmaceutically acceptable carrier.

Injectables can be prepared in conventional forms, either as liquid solutions or suspensions, solid forms suitable for solution or suspension in liquid prior to injection, or as emulsions. Alternatively, one may administer the heterologous agent and the cell membrane fusion protein or a functional fragment or derivative thereof in a local rather than systemic manner, for example, in a depot or sustained-release formulation. Further, the heterologous agent can be delivered adhered to a surgically implantable matrix (e.g., as described in U.S. Patent Publication No. 2004-0013645). The heterologous agent and the cell membrane fusion protein or a functional fragment or derivative thereof disclosed herein can be administered to the lungs of a subject by any suitable means, optionally by administering an aerosol suspension of respirable particles comprised of the heterologous agent, which the subject inhales. The respirable particles can be liquid or solid. Aerosols of liquid particles comprising the heterologous agent may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the heterologous agent may likewise be produced with any solid particulate medicament aerosol generator, by techniques known in the pharmaceutical art.

In certain embodiments, the heterologous agent and cell membrane fusion protein or a functional fragment or derivative thereof are administered to a subject in need thereof as early as possible in the life of the subject, e.g., as soon as the subject is diagnosed with a disease or disorder. In some embodiments, the method are carried out on a newborn subject, e.g., after newborn screening has identified a disease or disorder. In some embodiments, methods are carried out on a subject prior to the age of 10 years, e.g., prior to 1, 2, 3, 4, 5, 6, 7, 8, 9, or 10 years of age. In some embodiments, the methods are carried out on juvenile or adult subjects after the age of 10 years. In some embodiments, the methods are carried out on a fetus in utero, e.g., after prenatal screening has identified a disease or disorder. In some embodiments, the methods are carried out on a subject as soon as the subject develops symptoms associated with a disease or disorder. In some embodiments, the methods are carried out on a subject before the subject develops symptoms associated with a disease or disorder, e.g., a subject that is suspected or diagnosed as having a disease or disorder but has not started to exhibit symptoms.

The heterologous agent and the cell membrane fusion protein or a functional fragment or derivative thereof may be administered to a subject by any route of administration found to be effective to increase introduction (e.g., transduction) efficiency of the heterologous agent into the host cell. The most suitable route will depend on the subject being treated and the disorder or condition being treated. In some embodiments, the heterologous agent and the cell membrane fusion protein or a functional fragment or derivative thereof are administered to the subject by a route selected from oral, rectal, transmucosal, intranasal, inhalation (e.g., via an aerosol), buccal (e.g., sublingual), vaginal, intrathecal, intraocular, intravitreal, intracochlear, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

In particular embodiments, more than one administration (e.g., two, three, four or more administrations) may be employed to achieve the desired level of gene expression over a period of various intervals, e.g., daily, weekly, monthly, yearly, etc.

The heterologous agent and the cell membrane fusion protein or a functional fragment or derivative thereof can be administered to tissues of the CNS (e.g., brain, eye) and may advantageously result in broader distribution of the heterologous agent than would be observed in the absence of the present invention.

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratusi anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The heterologous agent and the cell membrane fusion protein or a functional fragment or derivative thereof can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105:3458-3464), and/or direct intramuscular injection. In particular embodiments, the heterologous agent and the cell membrane fusion protein or a functional fragment or derivative thereof are administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the heterologous agent can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the agent to cross the endothelial cell barrier. In particular embodiments, the heterologous agent and the cell membrane fusion protein or a functional fragment or derivative thereof can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The heterologous agent and the cell membrane fusion protein or a functional fragment or derivative thereof can be delivered to cardiac muscle by intravenous administration, intra-arterial administration such as intraaortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

[Delivery to a target tissue can also be achieved by delivering a depot comprising the heterologous agent. In representative embodiments, a depot comprising the heterologous agent and the cell membrane fusion protein or a functional fragment or derivative thereof is implanted into skeletal, smooth, cardiac and/or diaphragm muscle tissue or the tissue can be contacted with a film or other matrix comprising the heterologous agent. Such implantable matrices or substrates are described in U.S. Pat. No. 7,201,898.

Administration can also be to a tumor (e.g., in or near a tumor or a lymph node). The most suitable route in any given case will depend on the nature and severity of the condition being treated and/or prevented and on the nature of the particular vector that is being used.

In some embodiments, the heterologous agent and the cell membrane fusion protein or a functional fragment or derivative thereof are administered by the same route. In other embodiments, the heterologous agent and the cell membrane fusion protein or a functional fragment or derivative thereof are administered, e.g., the cell membrane fusion protein or a functional fragment or derivative thereof is administered intravenously and the heterologous agent is administered locally to a target tissue or organ.

The heterologous agent and the cell membrane fusion protein or a functional fragment or derivative thereof may be delivered or targeted to any tissue or organ in the subject. In some embodiments, the heterologous agent and the cell membrane fusion protein or a functional fragment or derivative thereof are administered to, e.g., a skeletal muscle, a smooth muscle, the heart, the diaphragm, the airway epithelium, the liver, the kidney, the spleen, the pancreas, the skin, the lung, the ear, and the eye. In some embodiments, the heterologous agent and the cell membrane fusion protein or a functional fragment or derivative thereof is administered to a diseased tissue or organ, e.g., a tumor.

In general, the nucleic acid delivery vectors of the present invention can be employed to deliver a nucleic acid encoding a polypeptide or functional nucleic acid to treat and/or prevent any disease state for which it is beneficial to deliver a therapeutic polypeptide or functional nucleic acid. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

In particular embodiments, a heterologous agent and the cell membrane fusion protein or a functional fragment or derivative thereof are administered to skeletal muscle, diaphragm muscle and/or cardiac muscle (e.g., to treat and/or prevent muscular dystrophy or heart disease [for example, PAD or congestive heart failure]).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, nucleic acid delivery vectors permit the treatment and/or prevention of genetic diseases.

As a further aspect, the nucleic acid delivery vectors of the present invention may be used to produce an immune response in a subject. According to this embodiment, a nucleic acid delivery vectors comprising a nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the nucleic acid delivery vectors may be administered to a cell ex vivo and the altered cell is administered to the subject. The nucleic acid delivery vectors comprising the nucleic acid is introduced into the cell, and the cell is administered to the subject, where the nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation, in* IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof. In particular embodiments, the nucleic acid delivery vector or cell comprising the nucleic acid can be administered in an immunogenically effective amount, as described below.

The nucleic acid delivery vectors can also be administered for cancer immunotherapy by administration of a nucleic acid delivery vector expressing one or more cancer cell antigens (or an immunologically similar molecule) or any other immunogen that produces an immune response against a cancer cell. To illustrate, an immune response can be produced against a cancer cell antigen in a subject by administering a nucleic acid delivery vectors comprising a nucleic acid encoding the cancer cell antigen, for example to treat a patient with cancer and/or to prevent cancer from developing in the subject. The nucleic acid delivery vectors may be administered to a subject in vivo or by using ex vivo methods, as described herein. Alternatively, the cancer antigen can be expressed as part of the nucleic acid delivery vectors.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a nucleic acid delivery vectors and the cell membrane fusion protein or a functional fragment or derivative thereof. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., $\alpha$-interferon, $\beta$-interferon, $\gamma$-interferon, $\omega$-interferon, $\tau$-interferon, interleukin-1$\alpha$, interleukin-1$\beta$, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

The methods of the present invention find use in both veterinary and medical applications. Suitable subjects include avians, reptiles, amphibians, fish, and mammals. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease. Preferably, the subject is a human.

In some embodiments, the nucleic acid delivery vector and the cell membrane fusion protein or a functional fragment or derivative thereof are introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

The nucleic acid delivery vectors and the cell membrane fusion protein or a functional fragment or derivative thereof can further be administered to elicit an immunogenic response (e.g., as a vaccine). Typically, immunogenic compositions of the present invention comprise an immunogenically effective amount of nucleic acid delivery vector in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the nucleic acid delivery vector (e.g., viral vector) and the cell membrane fusion protein or a functional fragment or derivative thereof to be administered to a subject depend upon the mode of administration, the disease or condition to be treated and/or prevented, the individual subject's condition, the particular nucleic acid delivery vector, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units, optionally about $10^8$-$10^{15}$ transducing units.

In a representative embodiment, the invention provides a method of treating and/or preventing muscular dystrophy in a subject in need thereof, the method comprising: administering a treatment or prevention effective amount of a heterologous agent and the cell membrane fusion protein or a functional fragment or derivative thereof to a mammalian subject, wherein the heterologous agent comprises a nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the heterologous agent and the cell membrane fusion protein or a functional fragment or derivative thereof can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional nuclei acid (e.g., functional RNA, e.g., RNAi, microRNA, antisense RNA) that normally circulates in the blood or for systemic delivery to other tissues to treat and/or prevent a disorder (e.g., a metabolic disorder, such as diabetes (e.g., insulin), hemophilia (e.g., Factor IX or Factor VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating and/or preventing metabolic disorders are described above. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a heterologous agent and the cell membrane fusion protein or a functional fragment or derivative thereof to a subject (e.g., to skeletal muscle of a subject), wherein the heterologous agent comprises a nucleic acid encoding a polypeptide, wherein the metabolic disorder is a result of a deficiency and/or defect in the polypeptide. Illustrative metabolic disorders and nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering heterologous agent and the cell membrane fusion protein or a functional fragment or derivative thereof to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a heterologous agent and s cell membrane fusion protein or a functional fragment or derivative thereof to a mammalian subject, wherein the heterologous agent comprises a nucleic acid encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active bARKct, Pim-1, PGC-1a, SOD-1, SOD-2, EC-SOD, kallikrein, HIF, thymosin-β4, mir-1, mir-133, mir-206 and/or mir-208.

In particular embodiments, the heterologous agent and the cell membrane fusion protein or a functional fragment or derivative thereof may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The heterologous agent of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a heterologous agent encoding one or more neurotrophic factors.

Age-related macular degeneration involves both angiogenesis and retinal degeneration. This disorder can be treated by administering a heterologous agent encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the heterologous agent. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a heterologous agent of the invention to treat a pituitary tumor. According to this embodiment, the heterologous agent encoding somatostatin (or an active fragment thereof) and the cell membrane fusion protein or a functional fragment or derivative thereof are administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins as are known in the art.

In particular embodiments, the heterologous agent can comprise a secretory signal as described in U.S. Pat. No. 7,071,172.

In representative embodiments of the invention, the heterologous agent and the cell membrane fusion protein or a functional fragment or derivative thereof are administered to the CNS (e.g., to the brain or to the eye). The heterologous agent and the cell membrane fusion protein or a functional fragment or derivative thereof may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The heterologous agent and the cell membrane fusion protein or a functional fragment or derivative thereof may also be administered to different regions of the eye such as the retina, cornea and/or optic nerve.

The heterologous agent and the cell membrane fusion protein or a functional fragment or derivative thereof may be delivered into the cerebrospinal fluid (e.g., by lumbar puncture) for more disperse administration of the heterologous agent. The heterologous agent may further be administered intravascularly to the CNS in situations in which the blood-brain barrier has been perturbed (e.g., brain tumor or cerebral infarct).

The heterologous agent and the cell membrane fusion protein or a functional fragment or derivative thereof can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the heterologous agent and the cell membrane fusion protein or a functional fragment or derivative thereof are administered in a liquid formulation by direct injection (e.g., stereotactic injection) to the desired region or compartment in the CNS. In other embodiments, the heterologous agent and the cell membrane fusion protein or a functional fragment or derivative thereof may be provided by topical application to the desired region or by intra-nasal administration of an aerosol formulation. Administration to the eye, may be by topical application of liquid droplets. As a further alternative, the heterologous agent may be administered as a solid, slow-release formulation (see, e.g., U.S. Pat. No. 7,201,898).

In yet additional embodiments, the heterologous agent and the cell membrane fusion protein or a functional fragment or derivative thereof can used for retrograde transport to treat and/or prevent diseases and disorders involving motor neurons (e.g., amyotrophic lateral sclerosis (ALS); spinal muscular atrophy (SMA), etc.). For example, the heterologous agent can be delivered to muscle tissue from which it can migrate into neurons.

In some embodiments, the cell membrane fusion protein or a functional fragment or derivative thereof may be administered by the same route as the heterologous agent, in in some embodiments, delivered by a different route or schedule than the heterologous agent.

Having described the present invention, the same will be explained in greater detail in the following examples, which are included herein for illustration purposes only, and which are not intended to be limiting to the invention.

EXAMPLES

As shown in the examples below, isolated FerA domains have been demonstrated to enhance AAV transduction efficiency, both in vitro and in vivo, in a species- and AAV serotype-independent manner, thus overcoming some of the limitations of previous AAV adjuvants.

Example 1: Methods

Cell lines: Huh7, HeLa, and C2C12 cells were maintained in Dulbecco's modified Eagle's medium (DMEM) supplemented with 10% (v/v) heat inactivated fetal bovine serum (FBS), and antibiotics (penicillin 100-U/mL and streptomycin 100-μg/mL). Human brain endothelial capillary hCMEC/D3 cells (Millipore Sigma, USA), as a model of human blood-brain barrier (BBB), were cultured as previously described in Zhang X., et al., "Blood-brain barrier shuttle peptides enhance AAV transduction in the brain after systemic administration," Biomaterials, 2018, 176:71-83. All cells were maintained at 37° C. in an atmosphere of 5% $CO_2$.

Expression and Purification of FerA domains: FerA samples were prepared as previously described in Harsini et al, *FerA is a Membrane Associating Four-Helix Bundle Domain in the Ferlin Family of Membrane-Fusion Proteins*, Sci Rep-Uk. 2019; 8. Briefly, human dysferlin FerA (hDys-FerA), human GFP-Dys-FerA (GFP-hDys-FerA), human myoferlin FerA (hMyo-FerA) and human or mouse otoferlin FerA (h/mOto-FerA) expression plasmids were transformed into chemically competent BL21 (DE3) cells using kanamycin as the selection antibiotic. One-liter TB (Terrific Broth) cultures with 50-μg/mL kanamycin utilizing IPTG chemical induction were used to grow up large volumes of cells. Cells were lysed using a microfluidizer and purified using affinity, ion exchange, and size-exclusion chromatography. All buffers were made the day of the experiment using fresh Milli-Q water. For Oto-FerA, 5 mM dithiothreitol (DTT) or 1 mM TCEP reducing agents were added to all buffers. Purity was assessed with SDS-PAGE Stain-Free gels (Bio-Rad, USA) for dysferlin and myoferlin. Due to the lack of tryptophan in Oto-FerA, coomassie staining was used for visualization. Protein concentration was measured by OD280 using extinction coefficients for hDys-FerA, GFP-hDys-FerA, and hMyo-FerA while a Bradford assay and reagent (Sigma Aldrich, USA) were used for h/mOto-FerA. FerA domains in a reducing reagent were exchanged with PD-10 desalting column (GE Healthcare Life Sciences, NJ, USA) and dissolved in Dulbecco's phosphate-buffered saline (DPBS). Finally, these proteins were stored at –80° C. in aliquots until ready to use.

Virus production: The detailed construction of the recombinant AAV full particles expressing luciferase, driven by the CBA promoter (AAV/luc), was reported previously in Zhang X., et al., "Blood-brain barrier shuttle peptides enhance AAV transduction in the brain after systemic administration," *Biomaterials,* 2018, 176:71-83. In short, the AAV transgene plasmid pTR/CBA-luc, AAV helper plasmid containing AAV Rep and Cap genes (pXR6, pXR8, or pXR9), and Ad helper plasmid pXX-680 were co-transfected into HEK293 cells. HEK293 cells were collected and lysed 48 hours (h) post-transfection. The supernatant was then subjected to CsCl gradient ultra-centrifugation. Fractions containing AAV were collected and viral titer was determined by real-time quantitative PCR (qPCR) using the Light Cycler 480 instrument with SYBR green (Roche, USA) and a pair of primers that were designed to bind to a homologous sequence on the inverted terminal repeat (ITR) region. The self-complementary AAV8 vector containing the hFIX cDNA (scAAV8/hFIX) was purchased from UNC Vector Core.

Cell toxicity assay: Huh7 cells were seeded in 96-well plates at a density of about $2.5 \times 10^4$ cells/well and incubated overnight at 37° C. Triplicate wells were treated with different concentrations of FerA. Cell toxicity assays were performed about 48 h after treatment using Celltiter 96 Aqueous one solution reagent (G3582, Promega, Madison, WI) according to the manufacturer's instructions. Cell viability was estimated by assessing the absorbance at 490 nm. All experiments were repeated at least 3 times.

In vitro transduction assay: At least 4-5 h before AAV/luc transduction, cells were seeded in 48-well plates at a density of about $1 \times 10^5$ cells per well. Different concentrations of FerA (0.05 µg and 0.5 µg) were incubated with AAV/luc at 4° C. for 2 h. After that, cells were transduced with 1×10⁹ vector genomes (vg) of AAV/luc virus or the incubated complex of virus and proteins. After 48 h, the cells were harvested and lysed. Luciferase activity was measured using the Promega Luciferase assay system based on the manufacturer's instructions (Promega, Madison, WI).

Streptavidin beads-based pull down assay: Biotinylated ligand/protein-based pull down assay was performed with Dynabeads® MyOne™ Streptavidin C1 beads (65001, Thermo Fisher Scientific, USA). For biotinylated ligand-based pull down, 1×10¹⁰ vg AAV9 was first incubated with/without 1-2 µg FerA for 2 h at 4° C. Then the CaptureSelect™ biotin anti-AAV9 conjugate (7103332100, Thermo Fisher Scientific, USA) was added and incubated for 1 h at room temperature (RT). After that, the complexes were isolated with 20 µl pre-washed Dynabeads® MyOne™ Streptavidin C1 beads for another 0.5 h at RT. Incubated complexes of AAV9 with Streptavidin C1 beads, Streptavidin C1 beads with FerA domains, AAV9 and FerA domains with C1 beads, and the biotin anti-AAV9 conjugate and FerA domains with C1 beads were included as controls. For biotinylated protein-based pull down, recombinant fusion protein GFP-hDys-FerA was first biotinylated by incubating GFP-hDys-FerA in 100 mM HEPES buffer (pH 7.3) containing N-hydroxysuccinimide ester (NHS)-water-soluble biotin (SP-1210-50, Vector Laboratories, CA, USA) for 2 h at RT, and then dialyzed according to the manufacturer's instructions. After that, the biotinylated GFP-hDys-FerA was mixed with AAV9 for 2 h at 4° C. Finally, the Streptavidin C1 beads were added and incubated for 0.5 h at RT. After stringent washing with DPBS four times, the final complex was boiled for 10 min in elution buffer and separated with 4-20% SurePAGE™ Bis-Tris gel (Gene Script, NJ, USA). The presence of bound FerA was analyzed by Western blotting with an anti-dysferlin antibody (HPA021945, Sigma Aldrich, USA), anti-myoferlin antibody (ab190264, Abcam, MA, USA), anti-otoferlin antibody (C-12) (sc-271092, Santa Cruz Biotechnology), or B1 mouse antibody. After that, membranes were extensively washed in DPBS containing 0.05% Tween-20 (DPBST), followed by incubation with horseradish peroxidase-conjugated goat anti-mouse IgG or anti-rabbit IgG (Thermo Fisher Scientific, USA) for 1 h at RT. Membranes were extensively washed in DPBST, and immunoblots were tested by Amersham ECL Western blotting detection kit and visualized with the Amersham imager 600 machine (GE Healthcare Life Sciences, NJ, USA).

Effect of FerA for AAV9 binding assay: 5×10⁵ Huh7 or Hela cells in 250 µl sera-free medium were suspended and incubated with 250 µl of medium containing AAV9/luc (10,000 vg/cell) or a complex of AAV9/luc and hDys-FerA previously incubated at 4° C. for 1 h with gentle shaking. For the binding assay, the cells were washed 3 times with cold DPBS to remove unbound virus particles and collected for total DNA preparation using the QIAamp DNA Blood Mini Kit (Qiagen, USA). Finally, genome DNA (gDNA) was quantified by qPCR with luciferase primers and reference GAPDH primers [40].

Transcytosis assay: Transcytosis assays were performed using the hCMEC/D3 cell line. Briefly, cells were seeded into Transwell®-COL collagen-coated membrane inserts (24-Well Permeable Support with 0.4 µm Pore Polycarbonate Membrane and 6.5 mm Inserts, Sigma Aldrich, USA) at a density of 5×10⁴ cells per well in EBM-2 cultured medium. The medium was changed every 2-3 days. After about 2 weeks, the cells were washed with DPBS and cultured in medium and treated with AAV9 alone or pre-incubated AAV9-0.5 µg hDys-FerA. The medium in the basal chamber was collected at different time points of 0.5 h, 2 h, 4 h, 6 h, and 24 h. Viral titers were calculated by qPCR according to established procedures using primers designed against the ITR region, discussed in Zhang X., et al., *Blood-brain barrier shuttle peptides enhance AAV transduction in the brain after systemic administration*, Biomaterials, 2018:176:71-83.

Histopathological and biochemical studies for liver toxicity: To investigate possible hepatotoxicity, mouse liver fragments in two groups with high doses (AAV9 and AAV9-hDys-FerA cohorts) were stained with hematoxylin and eosin (H&E) by the UNC Histology Research Core. Alanine aminotransaminase (ALT) activity and aspartate aminotransaminase (AST) activity in serum of injected mice by systemic administration were analyzed at different time points using ALT activity assay kit (ab105134, Abcam, Cambridge, MA) and AST activity assay kit (K753, Biovision, CA) according to the manufacturer's instructions.

Animal study: C57BL/6 female mice, at 5-6 weeks of age, were purchased from Jackson Laboratory (Bar Harbor, ME). 5-6 weeks of age FIX knockout (FIX−/−) female mice (Jin. D Y, et al., *Creation of a mouse expressing defective human factor IX, Blood*, 2004; 104:1733-9) were bred in house. All mice were randomly divided into groups of 5 animals each and maintained in a specific pathogen-free facility at UNC-Chapel Hill. All animal experimental procedures were approved by the UNC Institutional Animal Care and Use Committee. Mice were administered AAV-CBA/luc or scAAV8-hFIX incubated with FerA via retro-orbital injection or intramuscular injection. For mice receiving AAV-CBA/luc vectors, following intraperitoneal injection of D-luciferin substrate (Nanolight Pinetop, AZ), luciferase expression was imaged at the indicated time points using a Xenogen IVIS Lumina (Caliper Lifesciences, Waltham, MA). Bioluminescent images were analyzed using Living Image (PerkinElmer, Waltham, MA). For hemophilia B mice, at various time points post injection, blood samples were collected from the retro-orbital plexus into 1:9 parts 3.2% citrated sodium and stored at −80° C. for later FIX expression and function analysis. The viral titers were tested by qPCR. See, Zhang X., et al., *Blood-brain barrier shuttle peptides enhance AAV transduction in the brain after systemic administration*, Biomaterials, 2018:176:71-83.

Quantitation of luciferase expression in tissues: Animals utilized for imaging studies were sacrificed one-week after imaging work, and the tissues of the heart, liver, kidney, skeletal muscle, and brain were collected, minced, and homogenized in passive lysis buffer. The lysates were centrifuged at 12,000 g for 5 min to remove cellular debris. The supernatant was transferred to 96-well plates for luciferase activity analysis as described above. Total protein concentration in tissue lysates was measured using the Bradford assay (Sigma Aldrich, USA).

Measurement of AAV genome copy number in the tissues: Different minced tissues, or blood collected in different time points, were treated with Proteinase K and total genome DNA (gDNA) was isolated using the DNeasy blood & tissue kit (Qiagen, USA). The luciferase gene was measured by qPCR assay. The mouse GAPDH gene served as an internal control.

Detection of FIX concentration and activity: hFIX protein concentration in the plasma was measured by enzyme-linked immunosorbent assay (ELISA) as previously described (Wu Z, et al., *Optimization of Self-complementary AAV Vectors for Liver-directed Expression Results in Sustained Correc-*

*tion of Hemophilia B at Low Vector Dose*. Mol Ther. 2008; 16:280-9). The hFIX-specific one-stage FIX activity assay (hFIX-specific aPTT) was performed using a START 4 Coagulation Analyzer (Diagnostica Stago, Asnières, France) as described previously in Jin. D Y, et al., *Creation of a mouse expressing defective human factor IX*, Blood, 2004; 104:1733-9.

Statistical analysis: All quantitative data are presented as means±standard deviation (SD). Data were analyzed by either the two-tailed/sided Student's t-test or one-way ANOVA, and done using GraphPad Prism Version 6 software.

Example 2: Mouse Otoferlin FerA Enhances Transduction of Multiple AAV Serotypes In Vitro without Cytotoxicity To study whether the FerA domains from ferlin proteins have an effect on AAV transduction, the effect of the FerA from mouse otoferlin (mOto-FerA) on AAV transduction in vitro was investigated. AAV9/luc viruses (10,000 vg/cell) were incubated with mOto-FerA using different molecular ratios (AAV particle to FerA: 1:0, 1:20, 1:200, 1:2000, 1:20,000, and 1:200,000) at 4° C. for 2 h, and then the mixtures were applied onto Huh7 cells. After 48 h, cell cytotoxicity was tested with MTT assay and no significant cytotoxicity was observed regardless of FerA concentrations (FIG. 11A). Meanwhile, cell lysate was collected for luciferase analysis. The results showed that the incubated groups at the ratios of 1:20,000 and 1:200,000 significantly enhanced AAV9 transduction. In contrast, AAV9 transduction enhancement was not observed in non-incubated groups with different concentrations of mOto-FerA or incubated groups at the ratios of 1:20, 1:200, and 1:2000 (FIG. 11B). This result suggests that AAV transduction enhancement is results from the direct interaction of AAV virions with a certain amount of FerA molecules. Based on the above results, the effect of mOto-FerA with the ratios of 1:20,000 and 1:200,000 on different AAV serotypes transduction in different cell lines was investigated. It was found that transduction from AAV6, AAV8, and AAV9 was significantly increased in Huh7, hCMEC/D3, HeLa, and C2C12 cell lines (FIGS. 11C, 11D, 11E, and 11F). These results indicate that the mOto-FerA could enhance AAV transduction in a serotype-independent manner.

Figure 2B:
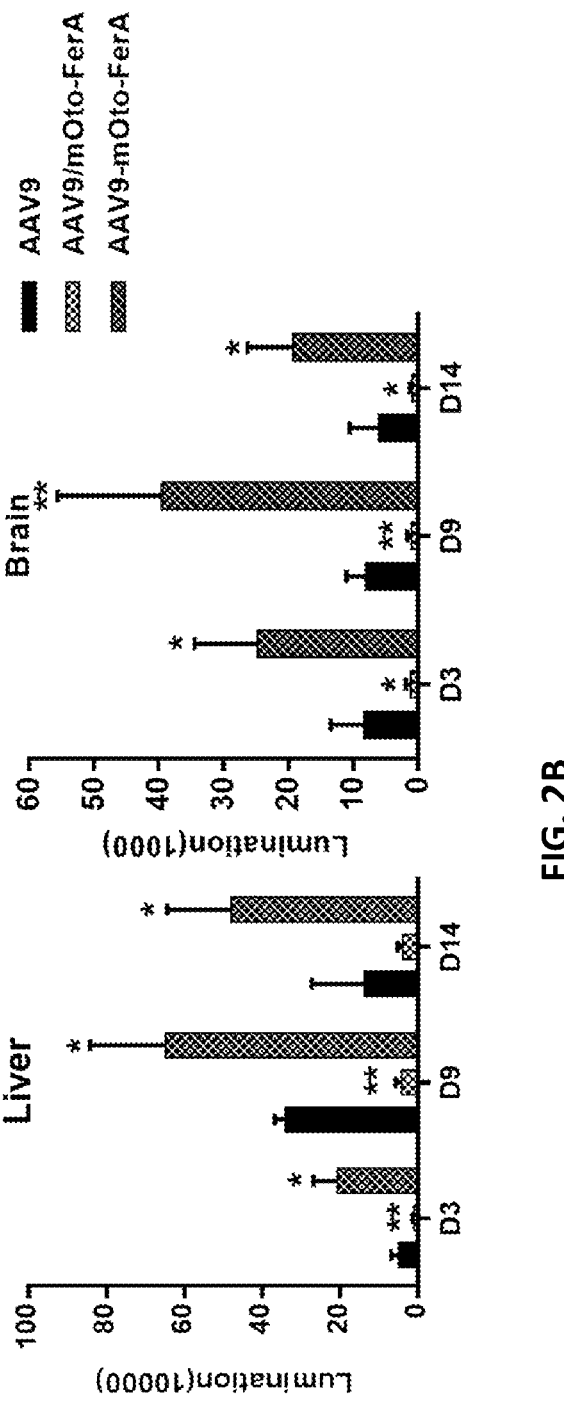
Figure 2C:
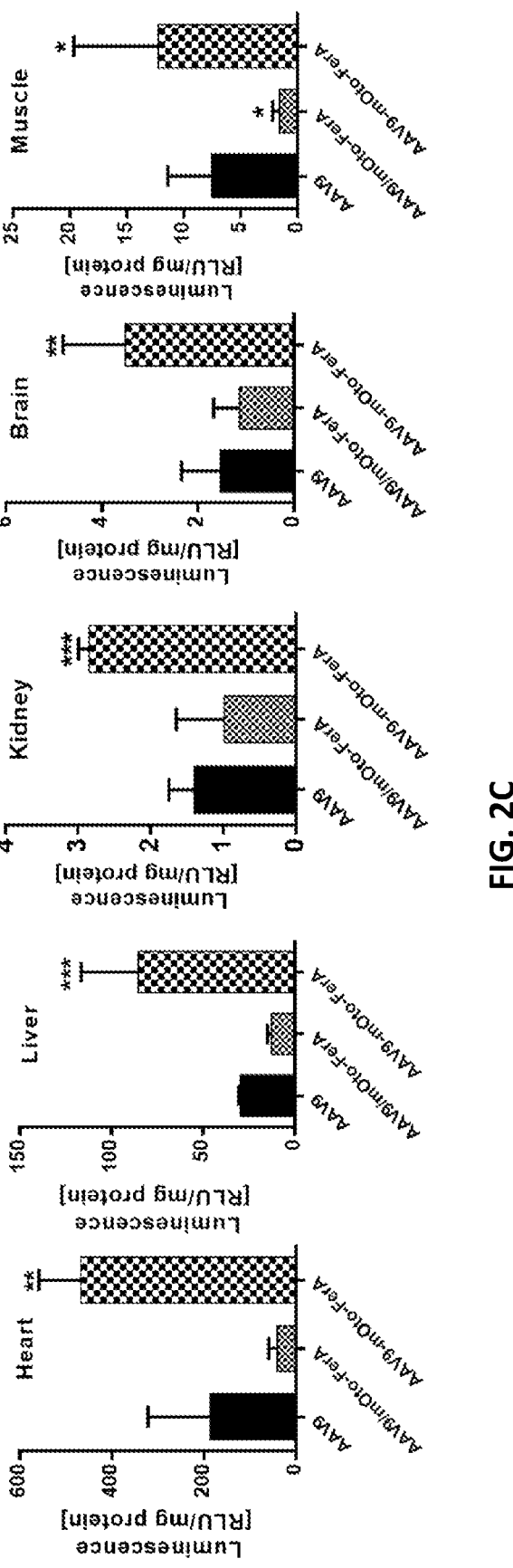
Figure 2D:
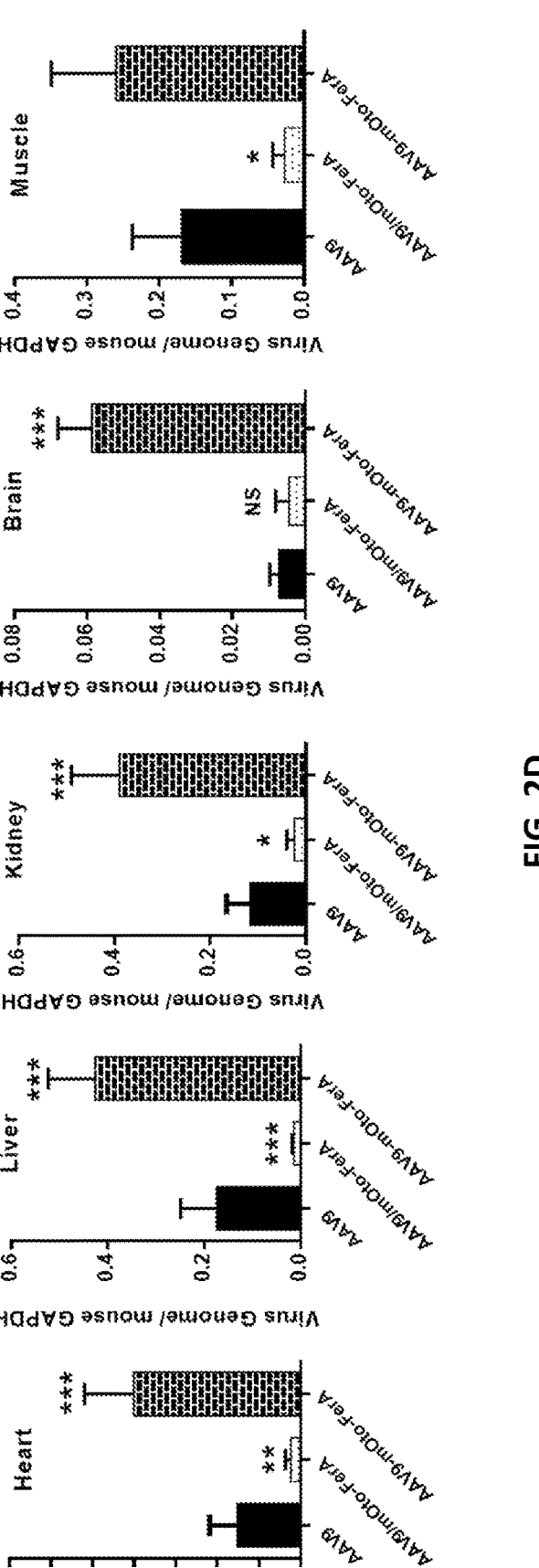
Figures 4A, 4B, 4C:
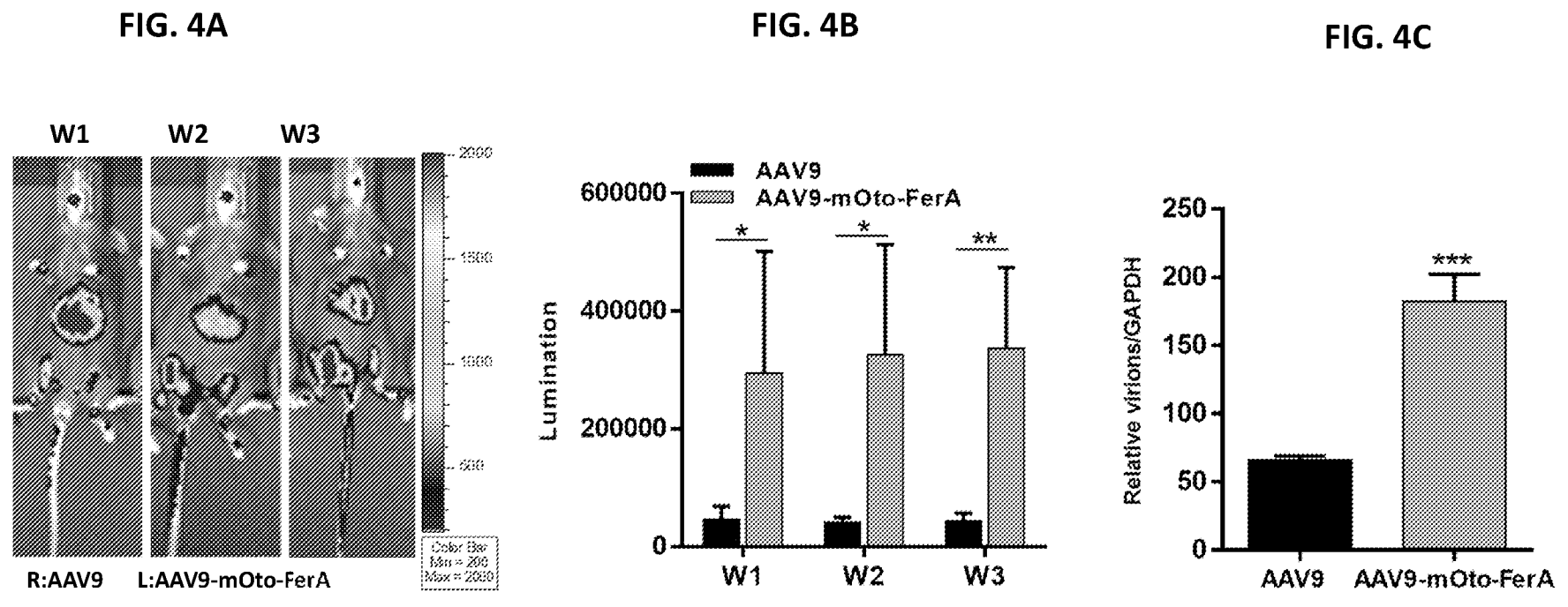

Example 3: Mouse Otoferlin FerA Enhances AAV Transduction In Vivo by Systemic or Intramuscular Administration The effect of mOto-FerA on AAV transduction in vivo was next investigated. AAV9 vectors pre-incubated with mOto-FerA at different molecular ratios were first administered in C57BL/6 mice, and the imaging was performed on day 1 and 3. Consistent with the results from cell lines in vitro, significantly increased transduction was achieved in mice with the ratios of 1:20,000 and 1:200,000 when compared to mice with the ratios of 1:0, 1:200 and 1:2000 (FIGS. 1A and 1B). To further confirm whether the AAV transduction enhancement required the direct interaction of AAV virions with FerA domains, three cohorts were designed: AAV9/luc vector (1×1010 vg) was incubated with 5 μg of mOto-FerA domain (AAV-mOto-FerA cohort, the ratio is 1:200,000) or PBS (AAV cohort) at 4° C. for 2 h and injected into C57BL/6 female mice via the retro-orbital vein. The third cohort was separately injected with 5 μg of mOto-FerA followed by AAV vectors immediately (AAV/mOto-FerA cohort). After 3, 7 or 9, and 14 days, images were taken. The results showed that the AAV9-mOto-FerA cohort significantly outperformed the other two cohorts for transgene expression in the whole body, especially the liver and brain (FIGS. 2A and 2B), which is consistent with the results observed in the different cell lines in vitro. Similar outcomes were seen on AAV6/luc and AAV8/luc serotypes (FIGS. 3A-3D). Interestingly, the non-incubation cohort AAV9/mOto-FerA or AAV8/mOto-FerA had significantly decreased transduction compared to the AAV9 or AAV8 group, respectively. At the end of the experiment, luciferase protein level and viral genome copy number in different tissues was evaluated. The results showed that the mOto-FerA generally increased luciferase protein expression and viral genome number in different tissues, which are in agreement with the imaging results (FIGS. 2C and 2D). Additionally, virus was administered intramuscularly with different AAV serotypes and it was found that the mOto-FerA could generally enhance the AAV transduction in the muscle (FIGS. 4A, 4B, 4D, 4E, 4G, and 4H). Accordingly, mOto-FerA increased viral genome number of multiple AAV serotypes in muscle (FIGS. 4C, 4F, and 4I). These data further support that mOto-FerA bolsters the AAV vectors transduction in a serotypes-nonspecific manner.

Example 4: Human FerA Domains Enhances AAV Transduction In Vitro

Given that mouse FerA may induce an unwanted immune response when applied in human studies, it was then investigated whether human-derived FerA domains were able to exert a similar enhanced effect on AAV transduction to mouse FerA. To this end, human FerA domains derived from dysferlin (hDys-FerA), myoferlin (hMyo-FerA), and otoferlin (hOto-FerA) at the doses of 0.05 μg and 0.5 μg were separately incubated with AAV9 vectors ($1 \times 10^9$ vg) at 4° C. for 2 h, then the complex was applied to different cell lines (Huh7, HeLa, and hCMEC/D3). The luciferase value was measured after 48 h treatment. The results showed that the hDys-FerA, hMyo-FerA, and hOto-FerA domains augmented the AAV9 transduction in all tested cell lines (FIGS. 12B, 12C, and 12D) under the premise of having no significant cytotoxicity (FIG. 12A).

Figures 5A, 5B:
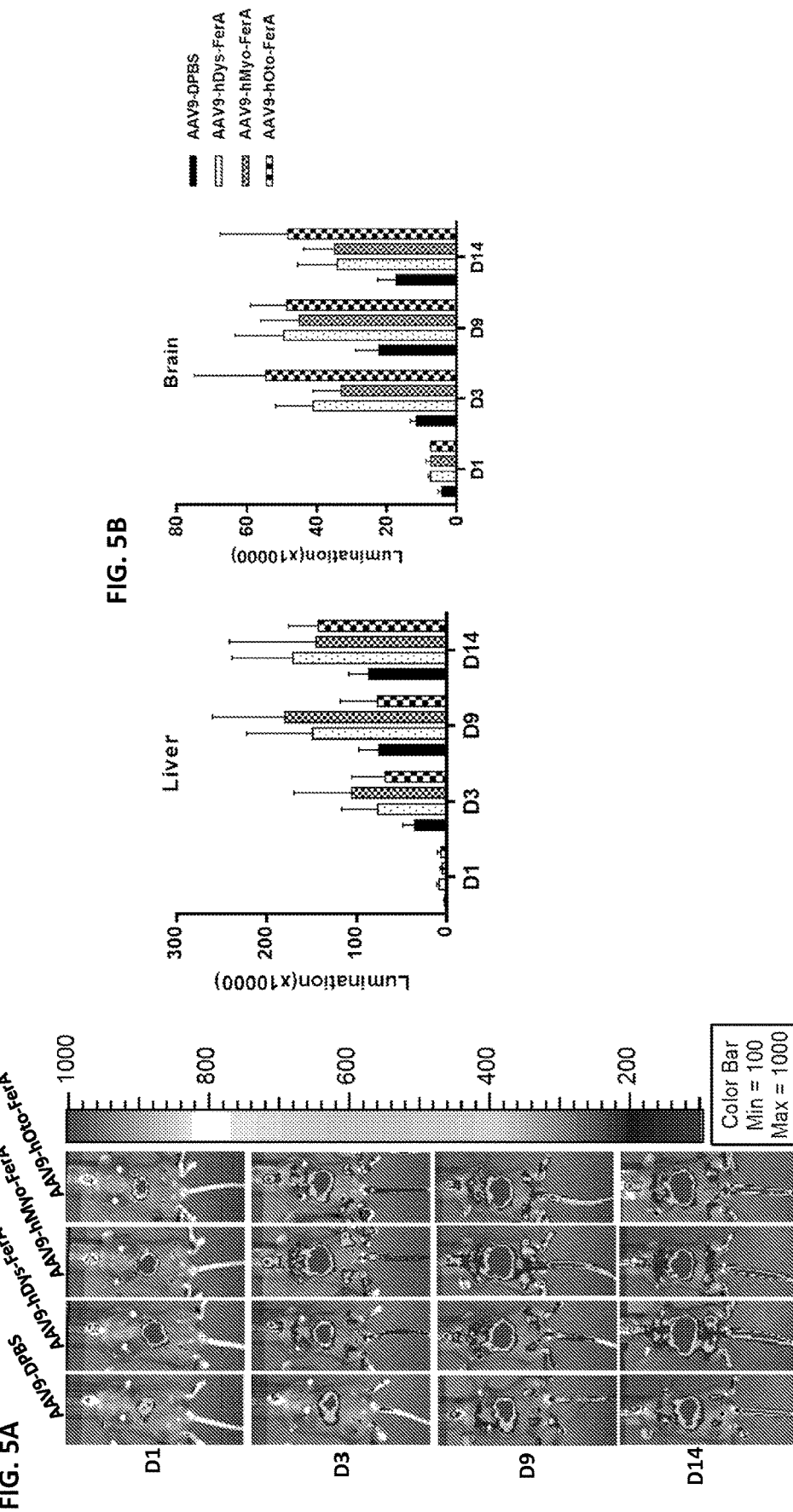
FIGS. 5A-5C show human FerA domains increased AAV9 transduction by systemic injections. AAV9/luc vectors were incubated with DPBS or hDys-/hMyo-/hOto-FerA domains for 2 h at 4° C. The complex was injected into female C57BL/6 mice by systemic administration. At different time points (D1, 3, 9, 14) post AAV application, images were taken for luminescence analysis (FIG. 5A). The average luciferase signal for liver and brain was calculated (FIG. 5B). The gene copy numbers in liver, brain, heart, kidney, and muscle were separately determined (FIG. 5C). The data of each group represent the average and SD from five mice. *$p<0.001$, $p<0.01$, and *$p<0.05$ compared to control mice with AAV9/luc treatment only.
Figure 5C:
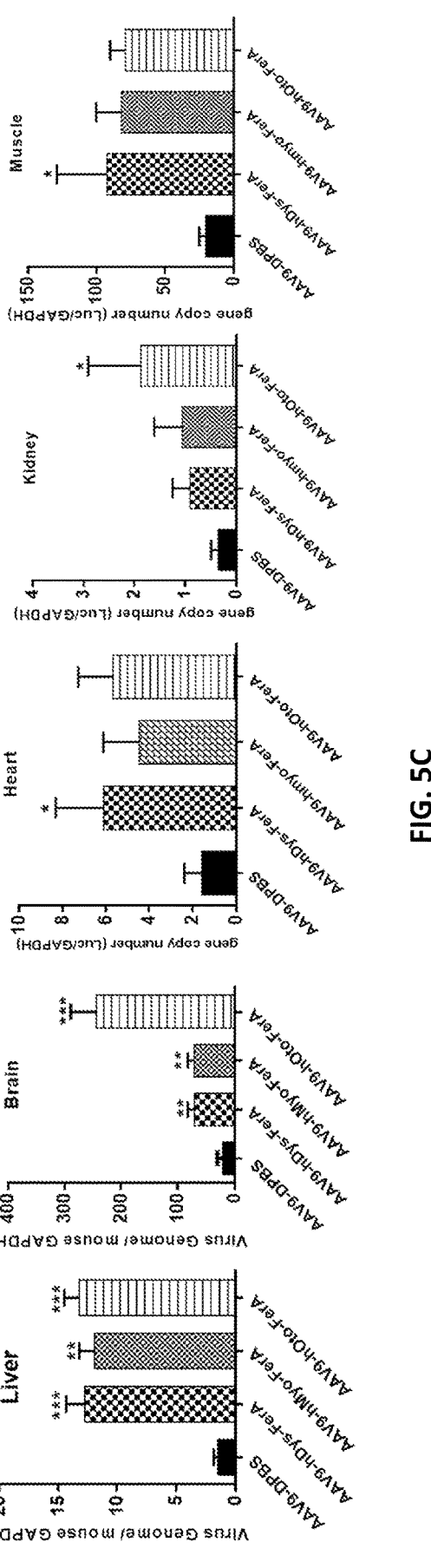
Figure 13A:
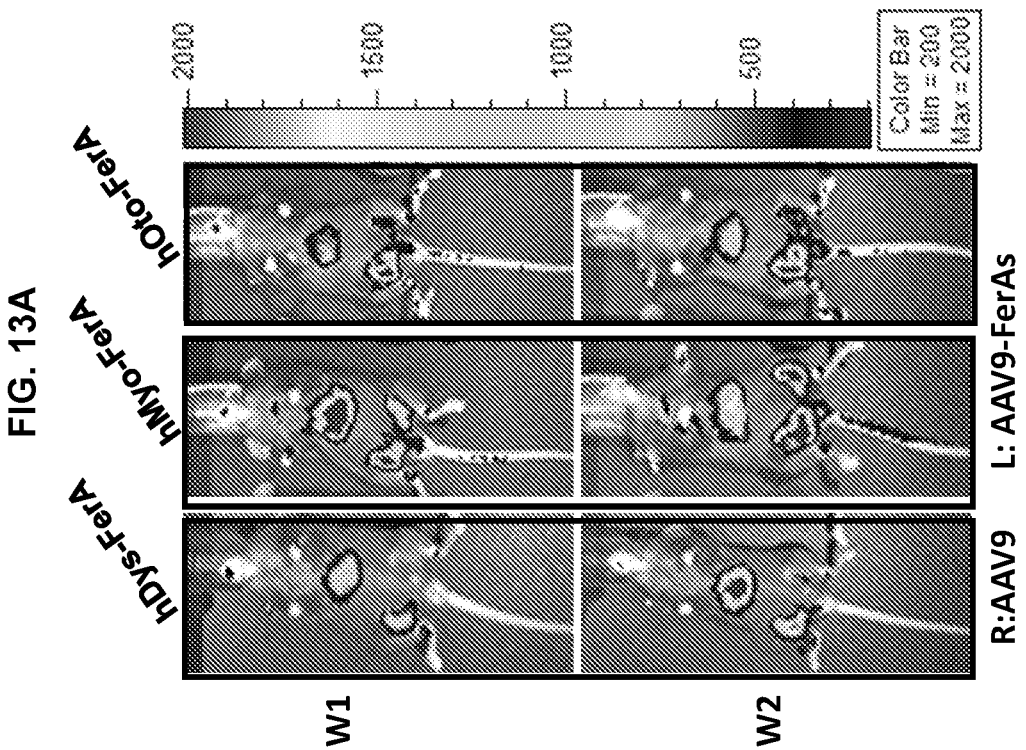
FIGS. 13A-13C shows that human FerA domains increased AAV muscle transduction. $2 \times 10^9$ particles of AAV9/luc were incubated with an equal volume of DPBS or 1 µg hDys- or hMyo- or hOto-FerA domain for 2 h at 4° C., then administered via intramuscular injection to muscles of both legs (R: right leg, L: left leg with face-up) in female C57BL/6 mice (n=5). Two weeks with 1-week-interval post AAV application, in vivo luminescence imaging was performed (FIG. 13A) and the photon signal of muscle was measured and calculated (FIG. 13B). The gene copy numbers in muscle were determined by qPCR (FIG. 13C). The data of each group represent the average and SD from five mice. **$p < 0.01$ and *$p < 0.05$ compared to control mice with AAV9/luc treatment only.
Figures 13B, 13C:
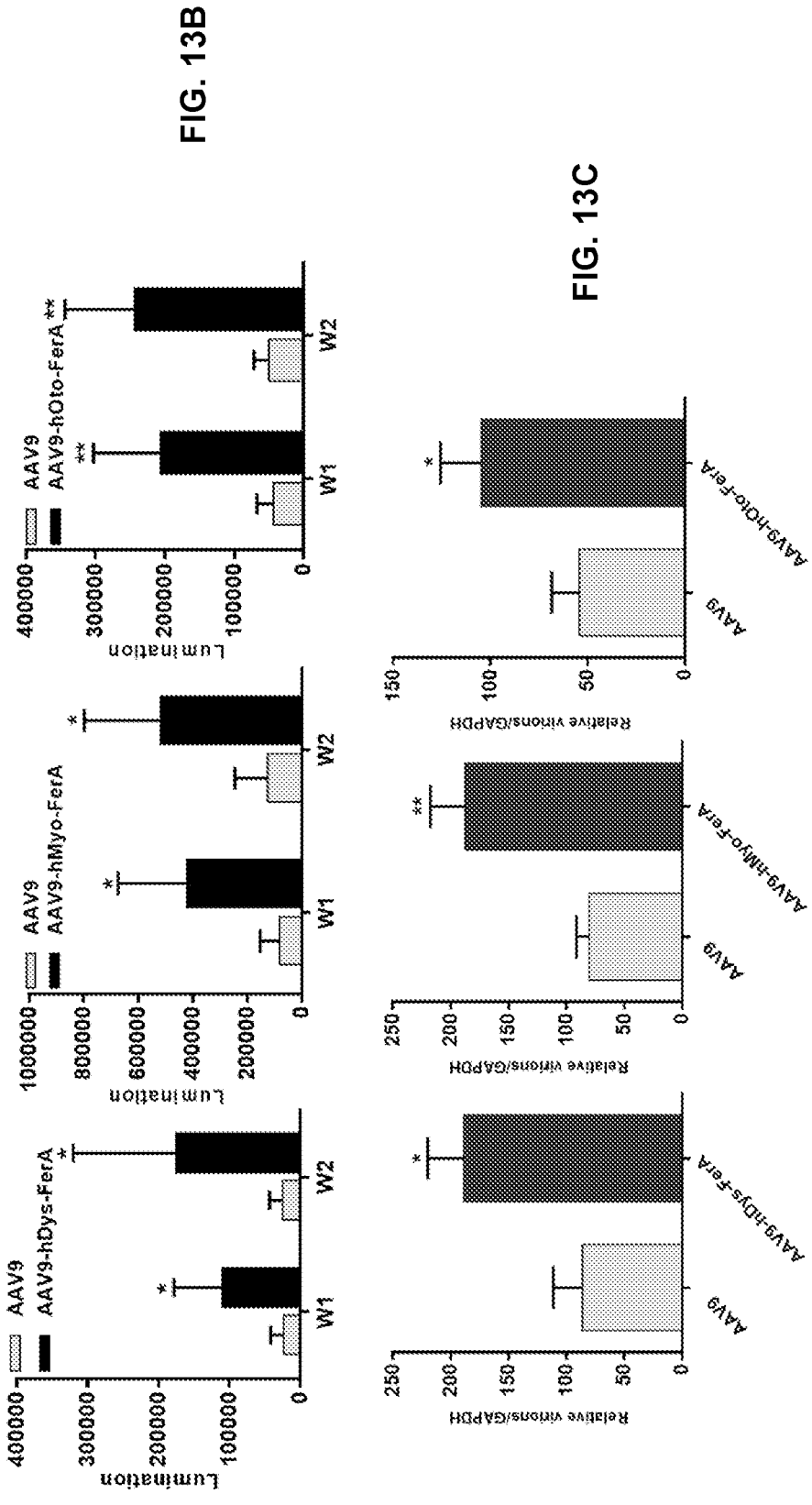

Example 5: Human FerA Domains Increase AAV9 Transduction In Vivo by Systemic or Intramuscular Administration To further validate the effect of human FerA domains on AAV transduction in vivo, C57BL/6 mice were randomly grouped, and systemically administered $1 \times 10^{10}$ particles of AAV9/luc alone or the complex of AAV9/luc pre-incubated with 5 μg of hDys-FerA, hMyo-FerA, or hOto-FerA domains. The results showed that, consistent with mOto-FerA (FIGS. 2A-2D and 3A-3D), all three human FerA domains resulted in vastly and significantly higher level of widespread luciferase expression when compared to control (FIGS. 5A and 5B). Similarly, higher AAV genomes were detected in tissues of mice receiving human FerA treatment (FIG. 5C). It is worth noting that the variable gene copy numbers from different human FerA domains were detected in the brain. The AAV genome copy number was much higher in the brain of mice treated with hOto-FerA than that with hDys-FerA and hMyo-FerA. This finding may be partially attributed to specific tissue localization of different ferlin proteins. After direct muscular injection, AAV9 vectors pre-incubated with FerA domains from three ferlin proteins induced a similar transduction enhancement (FIGS. 13A, 13B, and 13C).

Figure 6A:
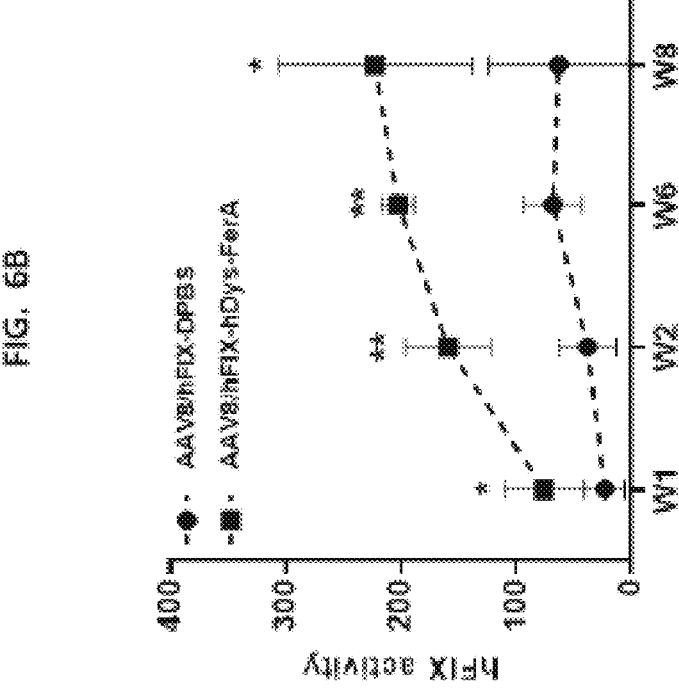
FIGS. 6A-6B show FerA improved phenotypic correction in FIX–/– hemophilic mice. $1 \times 10^{10}$ vg of pre-incubated AAV8-hFIX vectors with DPBS or hDys-FerA domain were administered in FIX–/– mice via retro-orbital injection. At 1, 2, 6 and 8 weeks after vector administration, plasma from FIX–/– mice were collected and isolated.
Figure 6B:
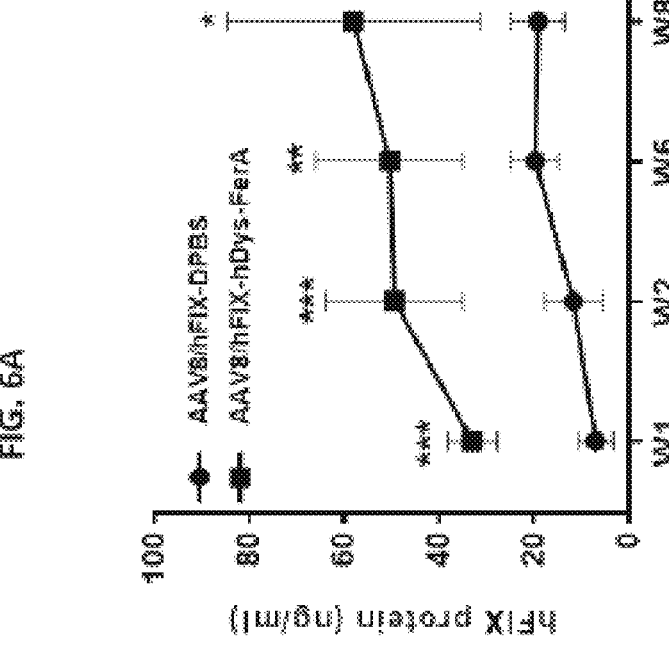

Example 6: FerA Significantly Improves Phenotypic Correction in Hemophilia B Mice after Systemic Injection of scAAV8/hFIX Vector The aforementioned findings demonstrated that FerA generally increases AAV transduction, which suggests similar transduction efficacy could be achieved with a lower dose of AAV vector coupled with the FerA domain. To apply this finding to treat a disease, scAAV8/hFIX or the complex scAAV8/hFIX-hDys-FerA was injected into adult female FIX-/- mice via retro-orbital injection at a dose of $1 \times 10^{10}$ vg per mouse. At different time points (week 1, 2, 6, and 8) after vector injection, we collected the plasma and tested the FIX expression and coagulation function. As predicted, FerA endowed a 4-fold higher hFIX protein expression and a better phenotypic correction in the hemophilic mice at different time points when compared to mice treated with scAAV8/hFIX (FIGS. 6A and 6B).

Example 7: Diverse FerA Domains Directly Interact with AAV9

The potential mechanism by which diverse FerA domains enhance transduction of multiple AAV serotypes in vitro and in vivo was next explored. The data from non-incubation of AAV virions with mOto-FerA suggested that direct interaction of AAV virions with FerA provides transduction enhancement in cell lines and in mice. To more definitely substantiate the observation, a series of Streptavidin C1 beads-based pull down assays was conducted. The Capture-Select™ biotin anti-AAV9 conjugate was added to the complex of pre-incubated AAV9 and hDys-, hMyo-, hOto-, or mOto-FerA domain for 1 h at RT, then Streptavidin C1 beads were added for another 0.5 h at RT. Single or combined incubation of AAV9 or FerA with C1 beads were included as controls. Potential AAV9-bound FerA was detected by Western blotting with corresponding anti-FerA antibodies. The results showed that FerA domains were able to bind to AAV9 effectively (FIGS. 7A, 7B, 7C, and 7D). It is also worth noting that the negatively-charged m/hOto-FerA domains slightly and inconspicuously bound to C1 beads, even with a stringent washing step during the pull-down assays (FIGS. 7C and 7D). The non-specific binding could be attributable to the propensity of Streptavidin C1 beads to non-specifically bind negatively charged molecules, according to the manufacturer's product information. On the other hand, AAV9 particles could also be pulled down by the biotin-labeled GFP-hDys-FerA domain (FIG. 7E). These results provide an alternative explanation for the in vivo observation noted above that the non-incubated group of mOto-FerA and AAV9 did not increase transduction, but on the contrary, significantly repressed AAV9 transduction efficiency.

Example 8: FerA Increases AAV9 Binding Ability to Target Cells

Figures 8A, 8B:
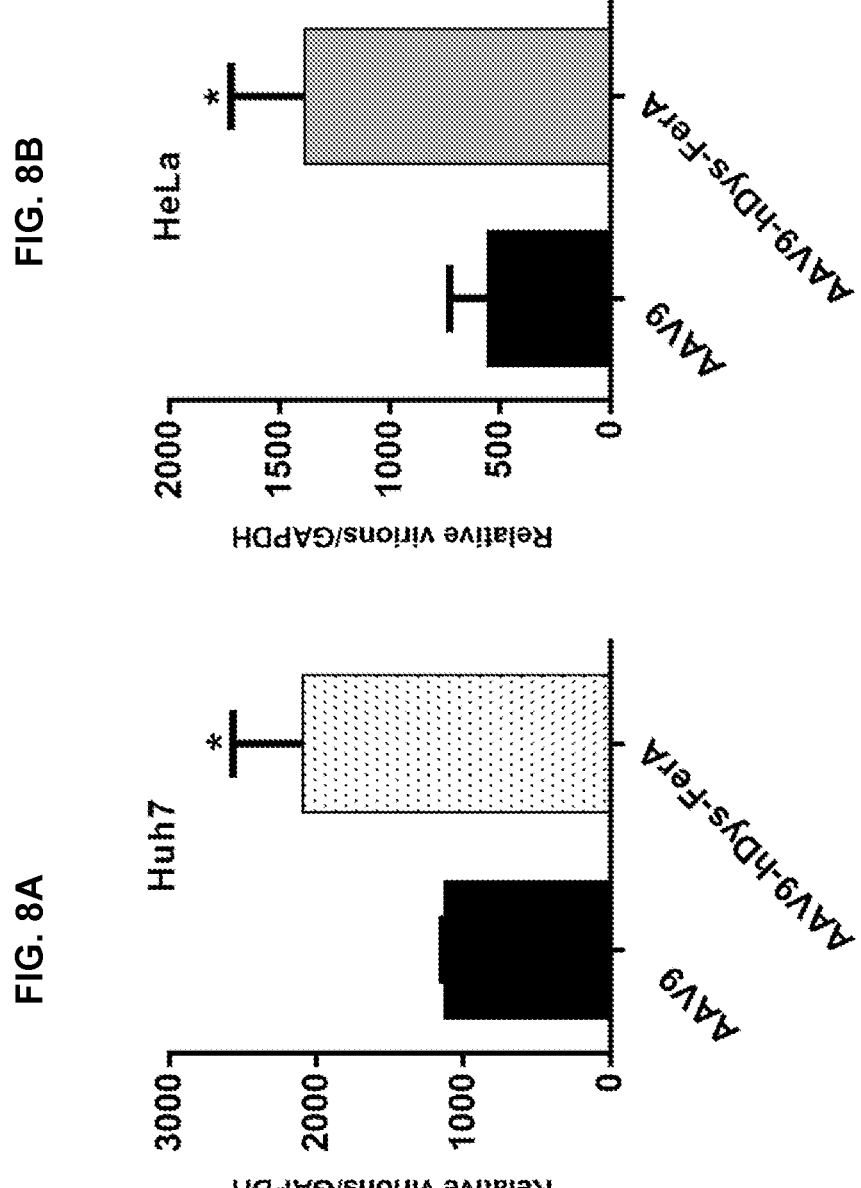
FIGS. 8A-8B show FerA increased AAV9 binding ability to target cells in vitro. The effect of FerA on the ability of AAV9 binding to cells was assessed in Huh7 (FIG. 8A) and HeLa (FIG. 8B) cells. The complex of AAV9 with DPBS or hDys-FerA domain was incubated with suspended cells for 1 h at 4° C. After that, cells were washed by centrifugation to get rid of unbound viruses. Finally, gDNA from virus bound to cells was extracted. The AAV9 genome copy number was measured and normalized to GAPDH. All treatments were performed in triplicate. Asterisks indicate statistical significance compared to the AAV9/luc alone treatment group (*$p<0.05$).

It was hypothesized that FerA might affect AAV binding ability to target cells. To examine this quantitatively, an AAV9 virion-binding assay was conducted in Huh7 and HeLa cells. After AAV9/luc only or a pre-incubated AAV9-hDys-FerA complex was allowed to attach during incubation at 4° C. for 1 h, unbound viruses were washed completely and gDNA was extracted. Finally, the viral gene copy numbers were determined by qPCR. The results showed that higher gene copy numbers were detected in the AAV9-hDys-FerA complex group (FIGS. 8A and 8B), which suggested that FerA dramatically expedited the binding of AAV virions to the cell surface.

Example 9: HDys-FerA Enhances AAV9 Transcytosis Ability

Figure 9B:
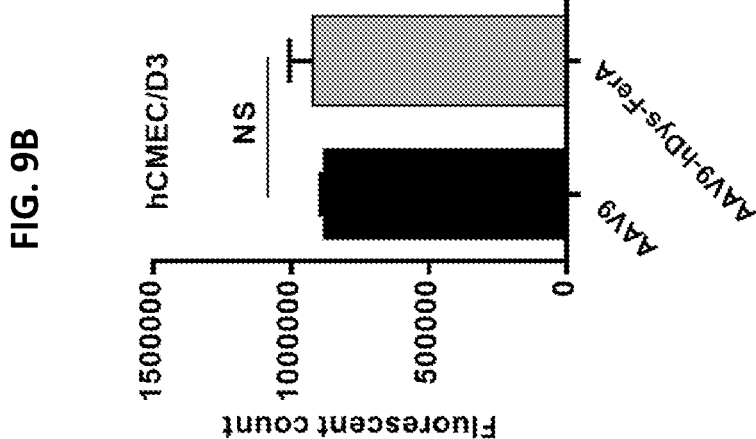
FIGS. 9A-9B show HDys-FerA enhanced the transcytosis ability of AAV9 in hCMEC/D3 cell line.
Figure 9A:
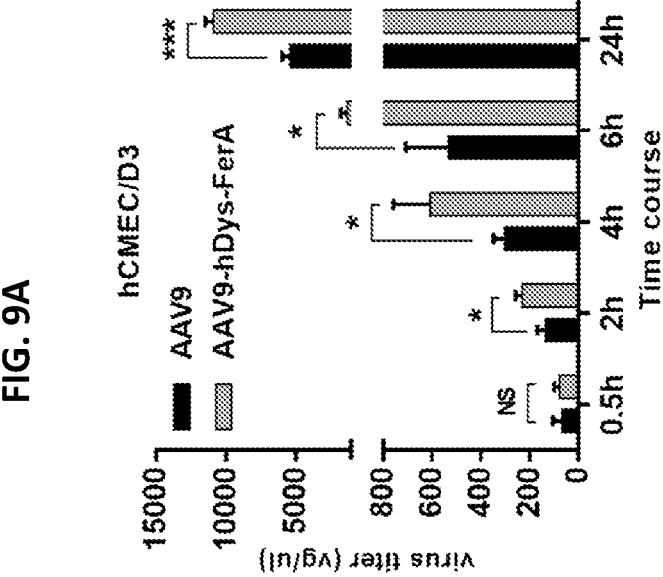

It has been demonstrated that enhanced global transduction was observed after systemic administration of AAV9 pre-incubated with FerA domains as described above (FIGS. 2A-2D, 3A-3D, and 5A-5C). These results suggest that FerA has the potential to increase the ability of AAV virions to cross the blood vascular barrier. To assess the effect of FerA on the ability of AAV9 to cross the endothelial cell layer, we carried out an in vitro endothelial cell permeability analysis in the brain microvascular endothelial cell model hCMEC/D3, as described in Weksler B., et al., *The hCMEC/D3 cell line as a model of the human blood brain barrier*, Fluid and barriers of the CNS, 2013; 10:16. Two groups were designed as follows: AAV9 vector incubated with DPBS (AAV9 cohort) and AAV9 vector incubated with hDys-FerA (AAV9-hDys-FerA cohort). Increased cell permeability was observed at different time points, especially at 24 h, in the AAV9-hDys-FerA cohort groups (FIG. 9A). The integrity of the endothelial monolayers was confirmed by FITC dextran fluorescence intensity analysis (FIG. 9B). These results indicate that FerA boosts AAV9 ability to penetrate the BBB via transcytosis, which further explains the observations of enhanced AAV transduction in the mouse brain in vivo (FIGS. 2A-2D and 5A-5C).

Figure 10B:
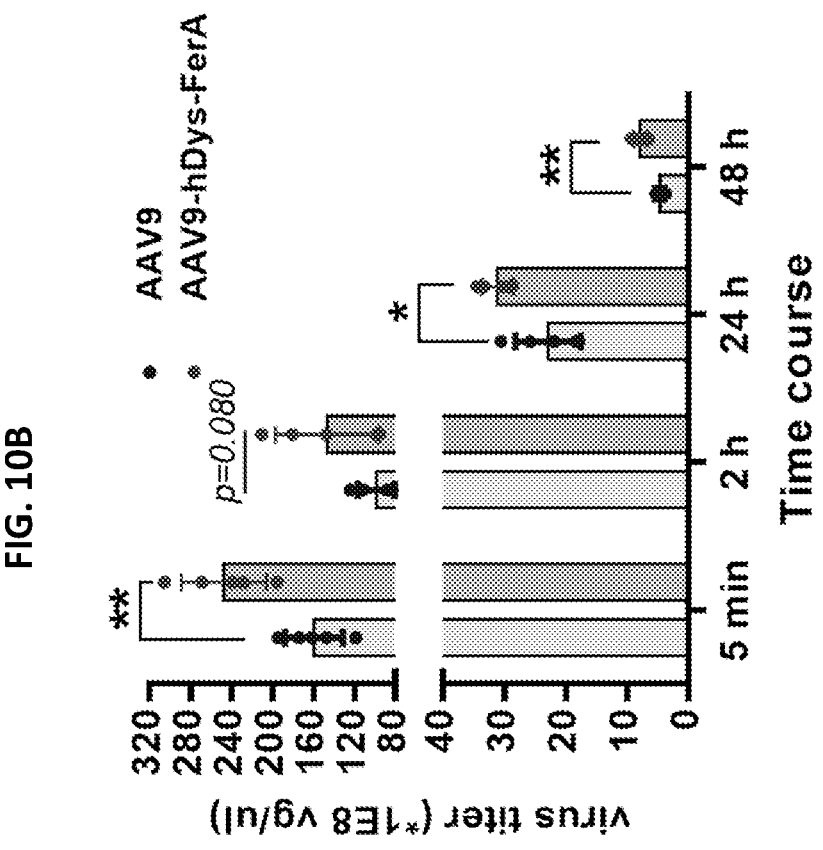
FIGS. 10A-10B show FerA decreased AAV9 clearance in the blood.
Figure 10A:
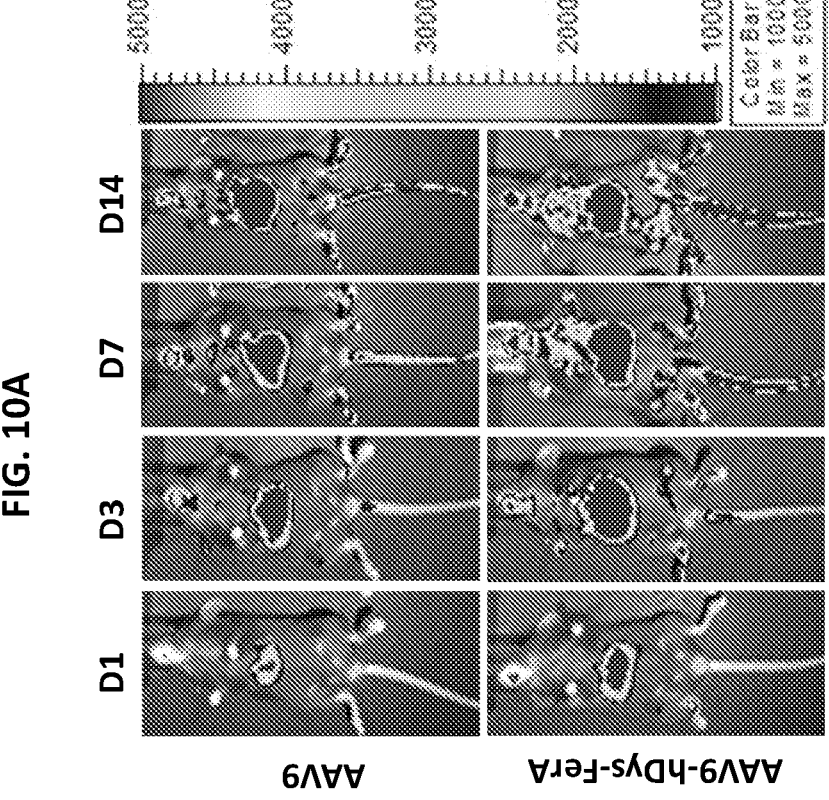

Example 10: FerA Decreases AAV9 Clearance in the Blood without Liver Cytotoxicity It was examined whether FerA can influence AAV virions clearance in the blood after systemic administration. C57BL/6 female mice were intravenously administered $1 \times 10^{11}$ vg per mouse of AAV9/luc or complex of virus pre-incubated with hDys-FerA (AAV9-hDys-FerA). Blood was collected at indicated time points (5 min, 2 h, 24 h, and 48 h) and the AAV genome copy number in the plasma was detected via qPCR. Consistent with the findings above, the hDys-FerA robustly enhanced AAV9 global transduction (FIG. 10A). The mice injected with AAV9-hDys-FerA exhibited higher AAV virions in circulation at both early (5 min) and later time points (48 h) after systemic administration than mice treated with AAV9 alone (FIG. 10B). This observation suggests that slow clearance of the AAV9 vector may increase the ability of AAV9 to cross the blood vascular barrier and enhance transduction in peripheral tissues after systemic administration. The potential of liver cytotoxicity after AAV transduction was also investigated by the detection of ALT and AST enzyme levels in the circulating blood and H&E staining. There was no obvious increase of ALT and AST levels in the plasma after systemic administration (FIGS. 14A and 14B). In addition, no pathological change was found in mouse livers of two groups via H&E staining (FIG. 14C).

In the current examples, it was demonstrated that isolated FerA domains derived from different ferlin proteins were able to serve as "native molecules" and augment divergent AAV serotypes transduction by systemic or intramuscular administration. Mechanism studies showed that the FerA domain could directly interact with AAV, increase AAV's binding activity on target cells, and its transcytosis ability. Meanwhile, it could delay the clearance of AAV particles from circulation to enhance AAV global transduction. FerA domains from four ferlin proteins of different species were capable of direct interaction with AAV and enhanced corresponding transduction. Importantly, due to the physical contact between FerA domains and AAV particles, the results translate from mouse to larger species, including human beings, and human-derived small proteins could be applied to patients who need systemic administration of AAV vectors with lower anticipated immune responses.

Different ferlin proteins have diverse tissue expression. For example, otoferlin is expressed in a wide range of tissues with high expression in the brain, vestibular system, and cochlea of the ear, which may explain the in vivo results with a higher virus gene copy number in the mouse brain of the hOto-FerA treated groups (FIG. 5C). Myoferlin shows ubiquitous expression, with high expression in developing skeletal muscle, cardiac muscle, and in the placenta (Davis D B, et al., *Myoferlin, a candidate gene and potential modifier of muscular dystrophy*. Hum Mol Genet. 2000; 9:217-26). Dysferlin is also ubiquitously expressed, with high expression in skeletal muscle, heart, and brain, implicating a role in surface membrane repair in muscle. Their distinct distribution in vivo may explain the ability of FerA domains to facilitate AAV transduction in different tissues (FIG. 5C). Herein, diverse FerA domains derived from different ferlin proteins could universally render multiple AAV serotypes with improved transduction.

While not being bound to any particular mechanism, the present data showed that the FerA domains could directly interact with AAV particles and increase their binding to targeted cells, which indicates that the direct interaction of FerA domains with AAV virions for high target cell binding capacity play a role in AAV transduction enhancement.

One notable phenomenon is that the groups with non-incubated mOto-FerA and AAV9 or AAV8 could not increase the transduction, but significantly inhibited the AAV transduction after systemic administration (FIGS. 2A-2D and FIG. 3B). Again, without being bound to any mechanism, it is a possibility that the excessive and dissociative FerA quickly and competitively occupies the AAV9 or AAV8 binding sites, leading to less AAV transduction. The other possibility is that liver cells interacting with extra FerA domains may influence their binding ability to AAV virions via unknown mechanisms.

Safety remains the utmost important concern for AAV-mediated gene therapy in preclinical and clinical trials. A recent study showed that high-dose intravenous administration of AAV led to extreme toxicity affecting the liver and motor neurons, with symptoms appearing within five days of treatment in nonhuman primates and piglets. FerA domains are naturally occurring intrinsic molecules in the human body, so, their use as accessory components for AAV transduction will exert a minimal impact on any immune response, especially a CTL response. Moreover, the solubility of isolated and purified FerA domain would likely not form significant amounts of complex aggregates, which would benefit its future manufacture and application.

The foregoing examples are illustrative of the present invention and are not to be construed as limiting thereof. Although the invention has been described in detail with reference to preferred embodiments, variations and modifications exist within the scope and spirit of the invention as described and defined in the following claims.

We claim:

1. A method of introducing a heterologous agent into a host cell, comprising contacting the host cell with the heterologous agent and a cell membrane fusion protein, wherein the cell membrane fusion protein is a functional fragment of a ferlin protein which is an isolated FerA domain.

2. The method of claim 1, wherein the host cell is contacted with the heterologous agent in vitro.

3. The method of claim 1, wherein the host cell is contacted with the heterologous agent in vivo.

4. The method of claim 1, wherein the heterologous agent is a nucleic acid delivery vector.

5. The method of claim 1, wherein the isolated FerA domain is a fragment of dysferlin (Fer1L1), otoferlin (Fer1L2), or myoferlin (Fer1L3).

6. The method of claim 5, wherein the cell membrane fusion protein comprises at least two different types of FerA domains.

7. The method of claim 1, wherein the method comprises:

combining the cell membrane fusion protein and the heterologous agent; and then contacting the host cell with the combined cell membrane fusion protein and the heterologous agent.

8. The method of claim 7, wherein the method comprises:

forming a complex between the cell membrane fusion protein and the heterologous agent; and then contacting the host cell with the complex.

9. The method of claim 7, wherein the cell membrane fusion protein and the heterologous agent are combined at a molecular ratio of at least 200:1 cell membrane fusion protein to heterologous agent.

10. The method of claim 9, wherein the cell membrane fusion protein and the heterologous agent are combined at a molecular ratio in a range of 20,000:1 to about 200,000:1 cell membrane fusion protein to heterologous agent.

11. The method of claim 4, wherein the nucleic acid delivery vector is a viral vector.

12. The method of claim 11, wherein the viral vector is an adeno-associated virus vector.

13. The method of claim 12, wherein the adeno-associated virus vector comprises a serotype selected from the group consisting of AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, equine AAV, ovine AAV, and a chimeric AAV vector.

14. The method of claim 1, wherein the isolated FerA domain is an isolated human FerA domain.

15. The method of claim 7, wherein the method further comprises incubating the combined cell membrane fusion protein and the heterologous agent prior to contacting the host cell with the combined cell membrane fusion protein and the heterologous agent.

16. A method of expressing a polypeptide or functional nucleic acid in a subject, comprising administering to the subject the heterologous agent and cell membrane fusion protein used in the method of claim 1, and expressing the polypeptide or functional nucleic acid in the subject.

17. A method of editing a gene in a subject, comprising administering to the subject the heterologous agent and cell membrane fusion protein used in the method of claim 1, thereby editing the gene in the subject.

18. A method of treating a disorder in a subject in need thereof, comprising administering to the subject the heterologous agent and cell membrane fusion protein used in the method of claim 1, thereby treating the disorder in the subject.

\* \* \* \* \*